(12) United States Patent
Hattori et al.

(10) Patent No.: US 8,703,968 B2
(45) Date of Patent: Apr. 22, 2014

(54) **COMPOUNDS FROM *ANTRODIA CINNAMOMEA* AND USE THEREOF**

(71) Applicant: Simpson Biotech Co., Ltd., Taoyuan County (TW)

(72) Inventors: Masao Hattori, Toyama (JP); Ali El-Halawany, Cairo (EG); Megumi Mizuno, Aichi-Ken (JP); Chia-Chin Sheu, Taoyuan County (TW)

(73) Assignee: Simpson Biotech Co., Ltd., Kuei Shan Hsiang, Taoyuan County (TW)

( * ) Notice: Subject to any disclaimer, the term of this patent is extended or adjusted under 35 U.S.C. 154(b) by 0 days.

(21) Appl. No.: 13/654,278

(22) Filed: Oct. 17, 2012

(65) Prior Publication Data

US 2013/0225649 A1 Aug. 29, 2013

Related U.S. Application Data

(60) Provisional application No. 61/547,891, filed on Oct. 17, 2011.

(51) Int. Cl.
*C07D 207/46* (2006.01)
*A61K 31/4015* (2006.01)

(52) U.S. Cl.
USPC .......................................... 548/542; 514/425

(58) Field of Classification Search
USPC .......................................... 548/542; 514/425
See application file for complete search history.

(56) References Cited

U.S. PATENT DOCUMENTS 7,109,232 B2 * 9/2006 Hattori et al. ................. 514/425

OTHER PUBLICATIONS

Liu et al.,"Hepatitis C NS3 protease inhibition by peptidyl-a-ketoamide inhibitors: kinetic mechanism and structure", 2004, pp. 207-216, vol. 421,. *Arch Biochem Biophys*.

Kakiuchi et al., "A high throughput assay of the hepatitis C virus nonstructural protein 3 serine proteinase ", 1999. pp. 77-84, vol. 80, *J Virol*.
Wu et al., "*Antrodia camphorata* ("niu-chang-chih"), new combination of a medicinal fungus in Taiwan", 1997, pp. 273-275, vol. 38, *Bot. Bull. Acad. Sin*.
Lin et al., "Factors affecting mycelial biomass and exopolysacharide production in submerged cultivation of *Antrodia cinnamomea* using complex media", 2007, pp. 2511-2517, vol. 98, *Bioresource Technology*.
Nakamura et al.,"Five new maleic and succinic acid derivatives from the mycelium of *Antrodia comphorata* and their cytotoxic effects on LLC tumor cell line", 2004,. pp. 46-48, vol. 67, *J Nat Prod*.
Han et al., "Protective effects of a neutral polysaccharide isolated from the mycelium of *Antrodia cinnamomea* on *Propionibacterium acnes* and lipopolysaccharide induced hepatic injury in mice", 2006, pp. 496-500, vol. 54, .*Chem Pharm Bull*.
Lee et. al., "*Antrodia camphorate* polysaccharides exhibit anti-hepatitis B virus effects", 2002, pp. 63-67, vol. 209 *FEMS Microbiol Lett*.
Berge et al., "Pharmaceutically Acceptable Salts,", 1977, pp. 1-19, vol. 66, J. Pharm. Sci.
C.M. Ma, et al. "Triterpenes from *Cynomorium songaricium*-analysis of HCV Protease Inhibitory Activity, Quantification and Content Change Under the Influence of Heating.", 2009, pp. 9-14, vol. 63, *J. Nat. Med*.
Y. Wei, et al., "Anti-HIV-1 Protease Triterpenoids from Stauntonia Obovatifoloala Hayata Subsp. Phytochemistry",2008, pp. 1875-1879, vol. 69.
D.T. Phuong, et al., "Inhibitory Effects of Antrodins A—E from *Antrodia cinnamomea* and Their Metabolites on Hepatitis C Virus Protease." 2009, pp. 582-584, vol. 23, Phytotherapy Research.
Lin et al., "Inhibition of dipeptidyl peptidase IV by fluoroolefin-containing N-peptidyl-O-hydroxylamine peptidomimetics" 1998, pp. 14020-14024, vol. 95, Proc. Natl. Acad. Sci. USA.
Stewart et al., "A concise synthesis of maleic anhydride and maleimide natural products found in *Antrodia* camphorate" 2007, pp. 2241-2244, vol. 48, Tetrahedron Letters.
Cheng et al., "Total synthesis of (±)-camphorataimides and (±)-himanimides by $NaBH_4/Ni(OAc)_2$ or Zn/AcOH stereoselective reduction." 2008, pp. 4347-4353, vol. 43, Tetrahedron.

* cited by examiner

*Primary Examiner* — Robert Havlin
(74) *Attorney, Agent, or Firm* — Muncy, Geissler, Olds & Lowe, P.C.

(57) ABSTRACT

The present invention relates to compounds from *Antrodia cinnamomea*. The present invention also relates to a composition and a method for treating or prophylaxis of hepatitis C virus (HCV) or human immunodeficiency virus (HIV) infection.

10 Claims, 7 Drawing Sheets

COMPOUNDS FROM *ANTRODIA CINNAMOMEA* AND USE THEREOF

FIELD OF THE INVENTION

The present invention relates to compounds from *Antrodia cinnamomea*. The present invention also relates to a composition and a method for treating or prophylaxis of hepatitis C virus (HCV) or human immunodeficiency virus (HIV) infection.

BACKGROUND OF THE INVENTION

It is estimated that approximate 3% of the world's population is infected with hepatitis C virus (HCV). In developed countries, chronic hepatitis C is the leading cause for cirrhosis, hepatocellular carcinoma, and liver transplantation. The protease of hepatitis C virus is required for the cleavage of viral nonstructural polyprotein to form the mature virus and represents one of the attractive therapeutic targets for developing antiviral agents against HCV (Liu et al., 2004; Hepatitis C NS3 protease inhibition by peptidyl-a-ketoamide inhibitors: kinetic mechanism and structure. *Arch Biochem Biophys* 421: 207-216; Kakiuchi et al., 1999 A high throughput assay of the hepatitis C virus nonstructural protein 3 serine proteinase. *J Virol* 80: 77-84).

Human immunodeficiency virus (HIV) is the virus known to cause acquired immunodeficiency syndrome (AIDS) in humans and AIDS presents special problems to the medical community which the present invention addresses. Without treatment, immunodeficiency viral infection is highly lethal. Indeed, AIDS is the leading cause of human death. In certain parts of the world, such as sub-Saharan Africa, at least 10% of all adults are believed to be infected with HIV, with the prevalence in many capital cities believed to be 35% or more. In the United States, an estimated 800,000 to 900,000 people are currently infected with HIV, with approximately 40,000 new infections occurring each year. Of the more than 700,000 individuals in the United States who were infected with HIV as of December 2000, 58% have died.

The use of herbal therapy and folk medicines has been known for thousands of years in China. In fact, records on the use of herbs date back to biblical times. However, only recently have scientists begun exploring the possible role for herbs in treatment of viral infections. For example, extracts from the root of the *Ecballium elaterium* have been used to treat HCV and HBV (EP 0793964 and U.S. Pat. No. 5,648,089). While research in the field of herbal medicines has increased, much remains to be learned about the effectiveness of such herbal remedies.

The fruiting body of *Antrodia cinnamomea* T. T. Chang & W. N. Chou (a taxonomic synonym of *Antrodia camphorate*, referring to Wu et al., 1997, *Antrodia camphorata* ("niu-chang-chih"), new combination of a medicinal fungus in Taiwan. *Bot. Bull. Acad. Sin.* 38: 273-275) is a highly valued folk medicine in Taiwan. It is used as an antidote and for diarrhea, abdominal pain, hypertension, itchy skin, and liver cancer. Some bioactive constituents from the fruiting body of *Antrodia cinnamomea* have been isolated and characterized as a series of polysaccharides, steroids, triterpenoids, and sesquiterpene lactone (Lin et al., 2007, Factors affecting mycelial biomass and exopolysaccharide production in submerged cultivation of *Antrodia cinnamomea* using complex media. *Bioresource Technology* 98: 2511-2517). In previous studies, five new maleic and succinic acid derivatives (Compound 1-5) are isolated from the mycelium of *Antrodia cinnamomea* (Nakamura et al., 2004, Five new maleic and succinic acid derivatives from the mycelium of *Antrodia comphorata* and their cytotoxic effects on LLC tumor cell line. *J Nat Prod* 67: 46-48).

U.S. Pat. No. 7,109,232 discloses Compounds 1-5 from *Antrodia cinnamomea* and their uses such as hepatoprotection, anti-inflammation or anti-tumor activity and preparation. PCT Publication No. WO 2009/094807 A1 discloses Compounds 1-10 from *Antrodia cinnamomea* and their use for treating or prophylaxis of hepatitis C virus infection.

Traditionally, the fruit body of *Antrodia cinnamomea* has been used for liver cancer (Lin E S, Chen Y H. 2007. Factors affecting mycelial biomass and exopolysaccharide production in submerged cultivation of *Antrodia cinnamomea* using complex media. *Bioresource Technology* 98: 2511-2517). Polysaccharides of *Antrodia cinnamomea* has been show to have hepatoprotective effect (Han et al., 2006b, Protective effects of a neutral polysaccharide isolated from the mycelium of *Antrodia cinnamomea* on *Propionibacterium acnes* and lipopolysaccharide induced hepatic injury in mice. *Chem Pharm Bull* 54: 496-500) and anti-hepatitis B virus activity (Lee et. al., 2002, *Antrodia camphorate* polysaccharides exhibit anti-hepatitis B virus effects. *FEMS Microbiol Lett* 209:63-67). Of the maleic and succinic acid derivatives, Compound 3 showed protective activity in *Propionicbacterium acnes* and lipopolysaccharide treated mice (Nakamura N, Five new maleic and succinic acid derivatives from the mycelium of *Antrodia comphorata* and their cytotoxic effects on LLC tumor cell line. *J Nat Prod* 67: 46-48). Quantitative analysis showed that Compound 3 was the most abundant compound of this chemical type in the mycelium with a content of ca. 5% of the dry weight of mycelia (Han et al., 2006a, Protective effects of a neutral polysaccharide isolated from the mycelium of *Antrodia cinnamomea* on *Propionibacterium acnes* and lipopolysaccharide induced hepatic injury in mice. *Chem Pharm Bull* 54: 496-500).

During the investigation for anti HCV agents from natural source, compounds isolated from *Antrodia cinnamomea* showed variable activities (PCT publication No. WO 2009/094807). The highest was compound 1 (0.9 µg/mL), compound 3 (2.9 µg/mL). Compound 2 shows low activity, although it is sharing the main nucleus with other compounds. Therefore a series of derivatives was carried out, in this study, for Compound 2 targeting to improve its activity as anti HCV protease agent. Also, a new isolated compound from *Antrodia cinnamomea* was investigated its activity as anti HCV or HIV-1 protease agent.

SUMMARY OF THE INVENTION

Figure 1:
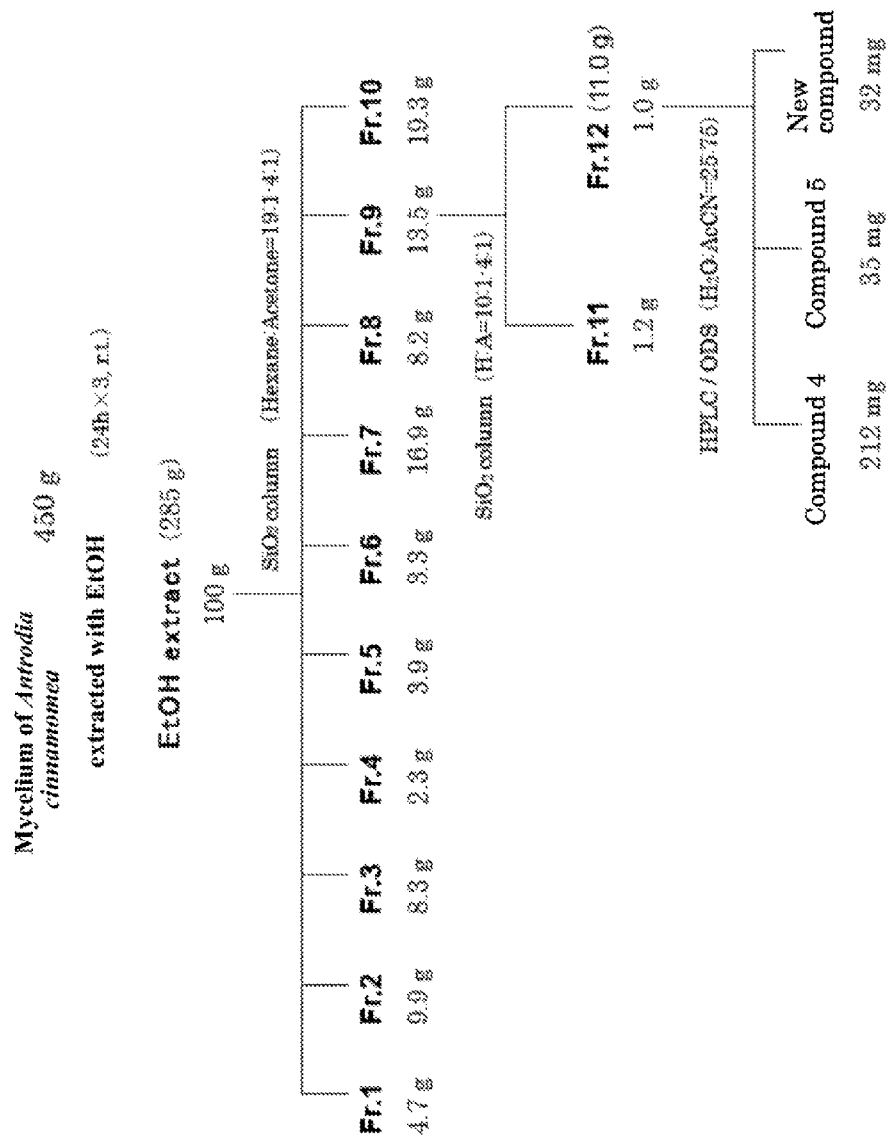
FIG. 1 shows the ingredient isolated from the EtOH extract of the mycelium of *Antrodia cinnamomea*.

Accordingly, an object of the present invention is to provide novel compounds from the mycelium of *Antrodia cinnamomea*.

Another object of the present invention is to provide a pharmaceutical composition for treating or prophylaxis of hepatitis C virus or human immunodeficiency virus infection, which comprises a compound of the present invention in an amount effective to attenuate infectivity of said virus, and a pharmaceutically acceptable carrier.

Further object of the present invention is to provide a method for treating or prophylaxis hepatitis C virus or human immunodeficiency virus infection which comprises administering to a subject in need thereof an effective amount of a composition comprising the compounds from the mycelium of *Antrodia cinnamomea*.

Additional embodiments, features, and advantages of the invention will be apparent from the following detailed description and through practice of the invention.

DETAILED DESCRIPTION OF THE INVENTION

For the sake of brevity, the disclosures of the publications, including patents, cited in this specification are herein incorporated by reference.

The terms "including", "containing" and "comprising" are used herein in their open, non-limiting sense.

Accordingly, the present invention also provides a compound of formula (I)

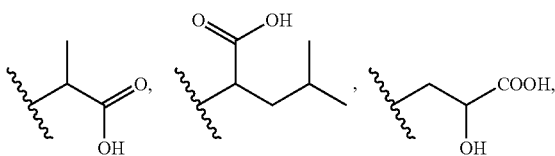

(I)

where $R_1$ is

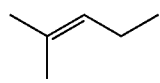

or H;

$R_2$ is selected from the groups as follows:

Group (A)

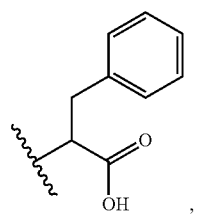

-continued

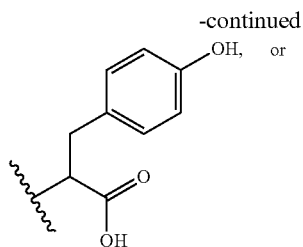

Group (B)

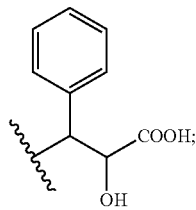

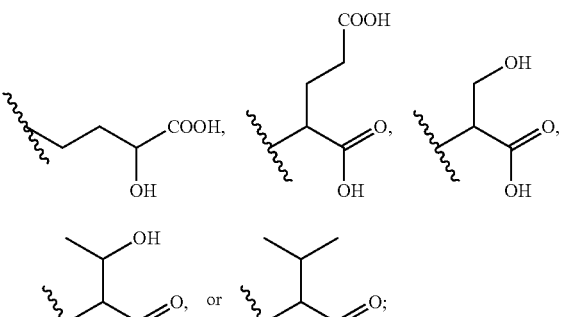

Group (C)

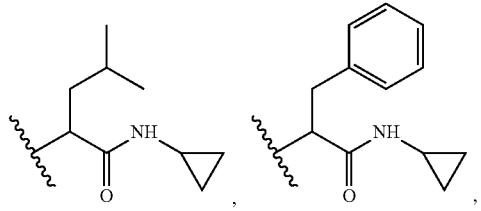

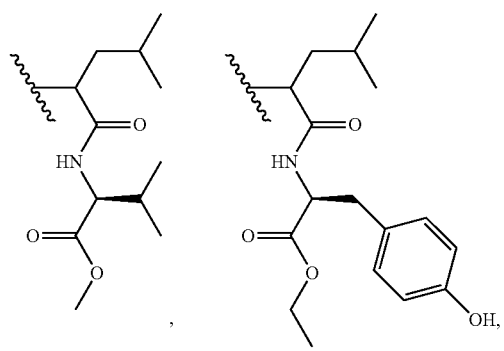

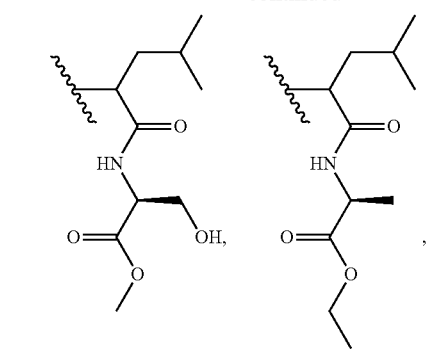
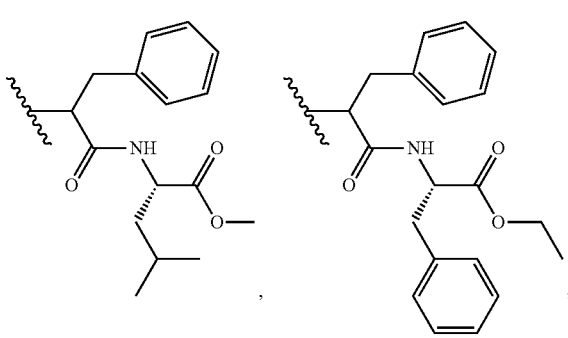
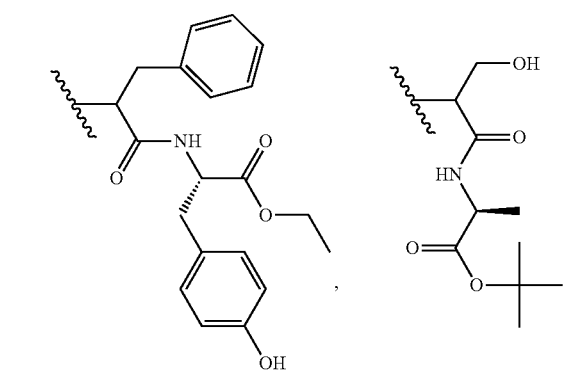
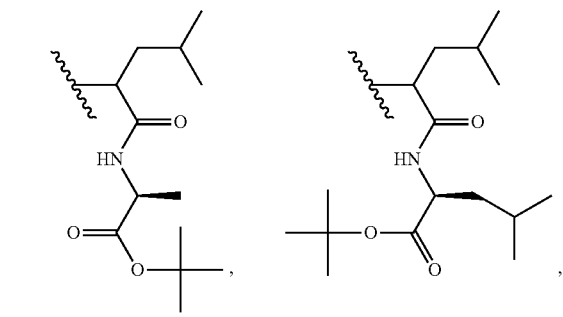
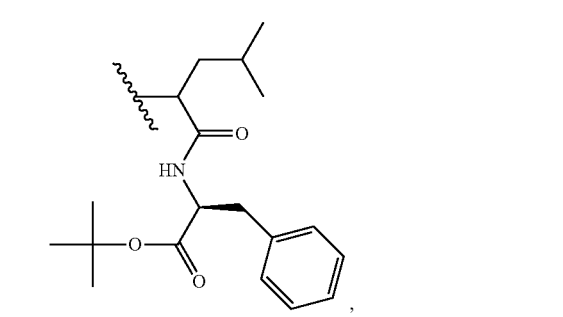
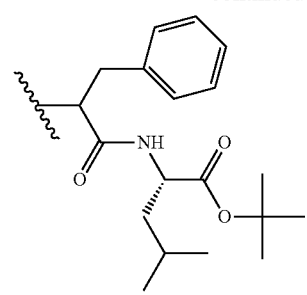
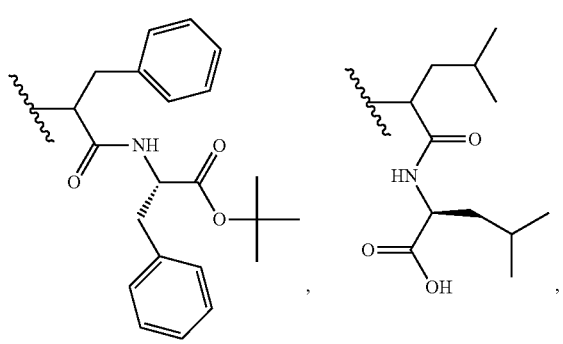
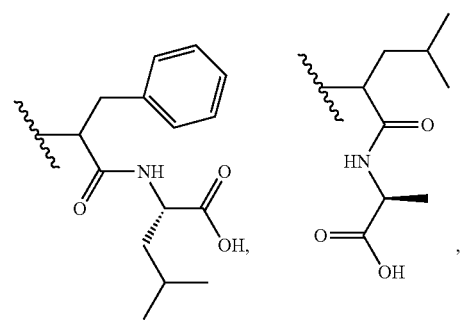
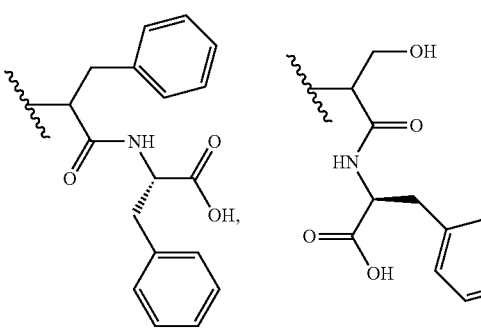
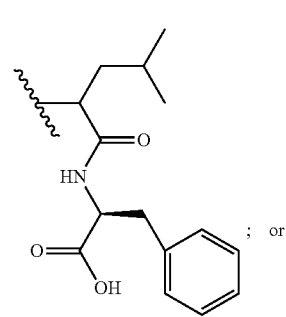 [SMILES: *C(CC(C)C)C(=O)N[C@@H](Cc1ccccc1)C(=O)O]

Group (D)
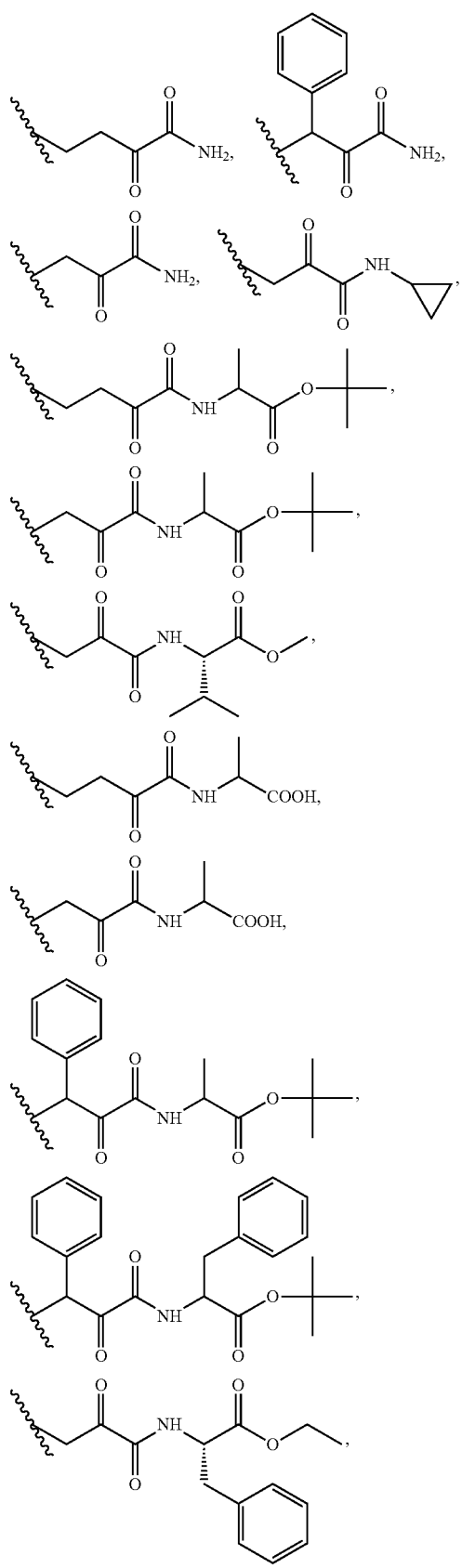
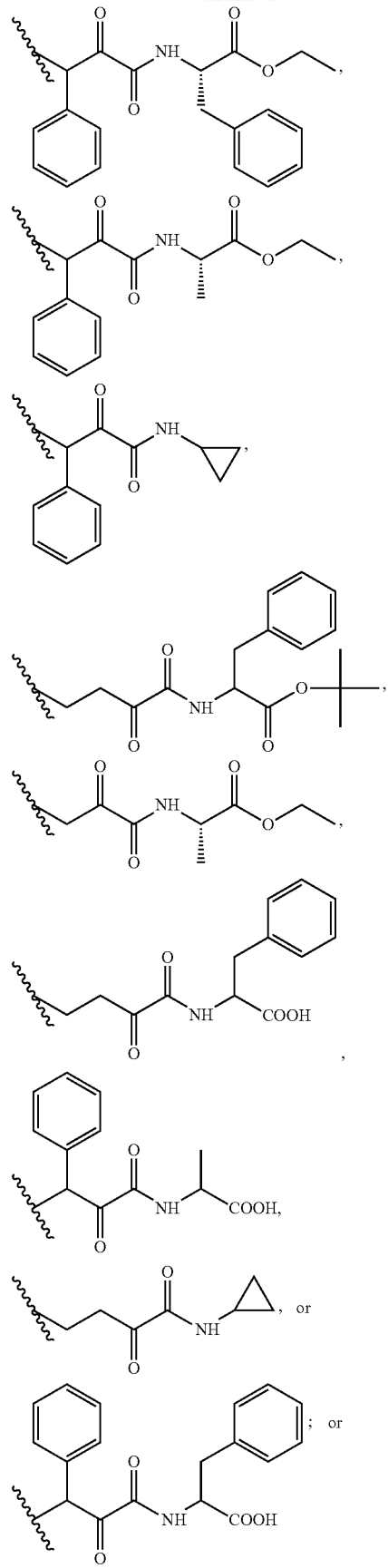

-continued
Group (E)
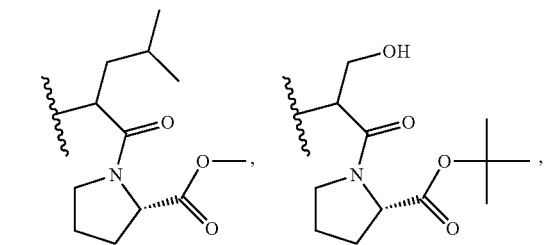
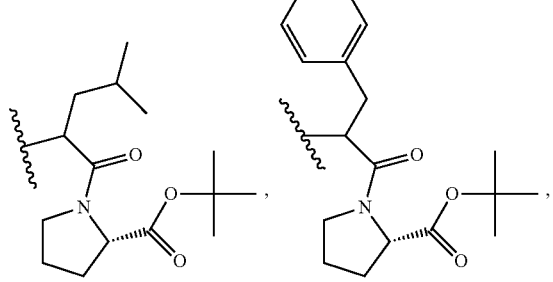
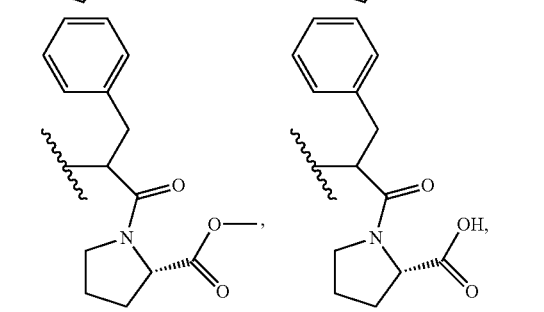
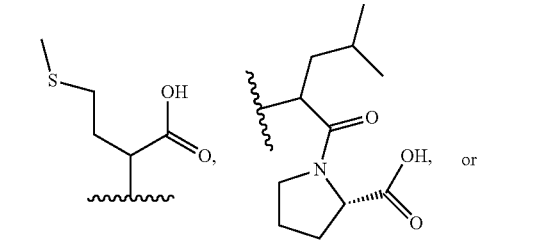
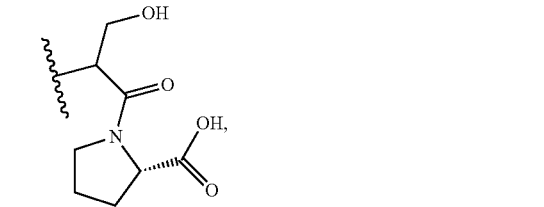
$R_3$ is $C_{1-10}$ alkyl, $C_{2-10}$ alkenyl, benzyl, or 4-(3-methyl-2-butenyloxy)phenyl, ⁓ denotes the place of connection, or pharmaceutically acceptable salts or prodrugs thereof.
Preferably, $R_1$ is
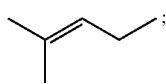;
$R_2$ is selected from the groups as follows:
Group (A)
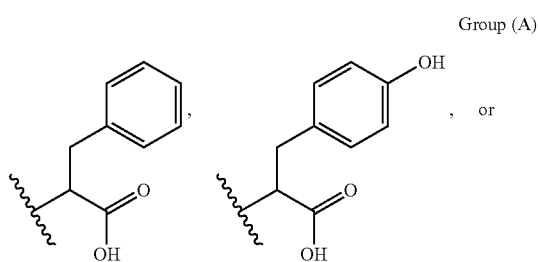
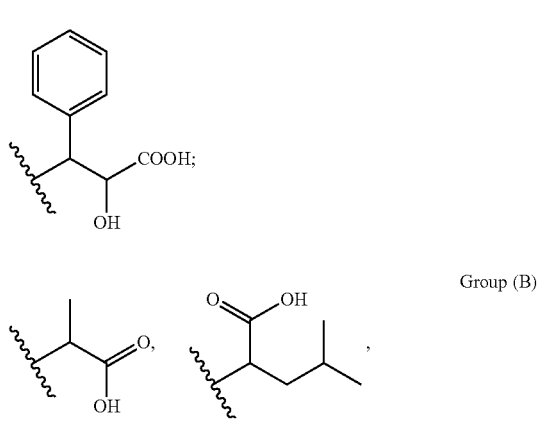
Group (B)
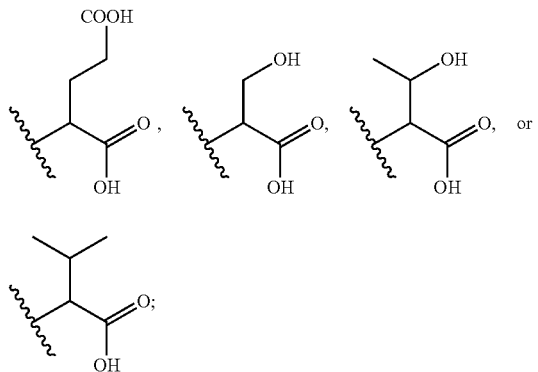
Group (C)
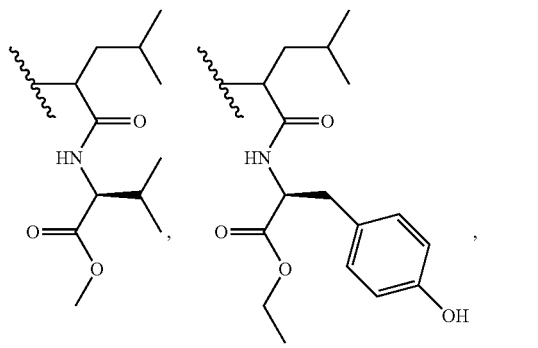

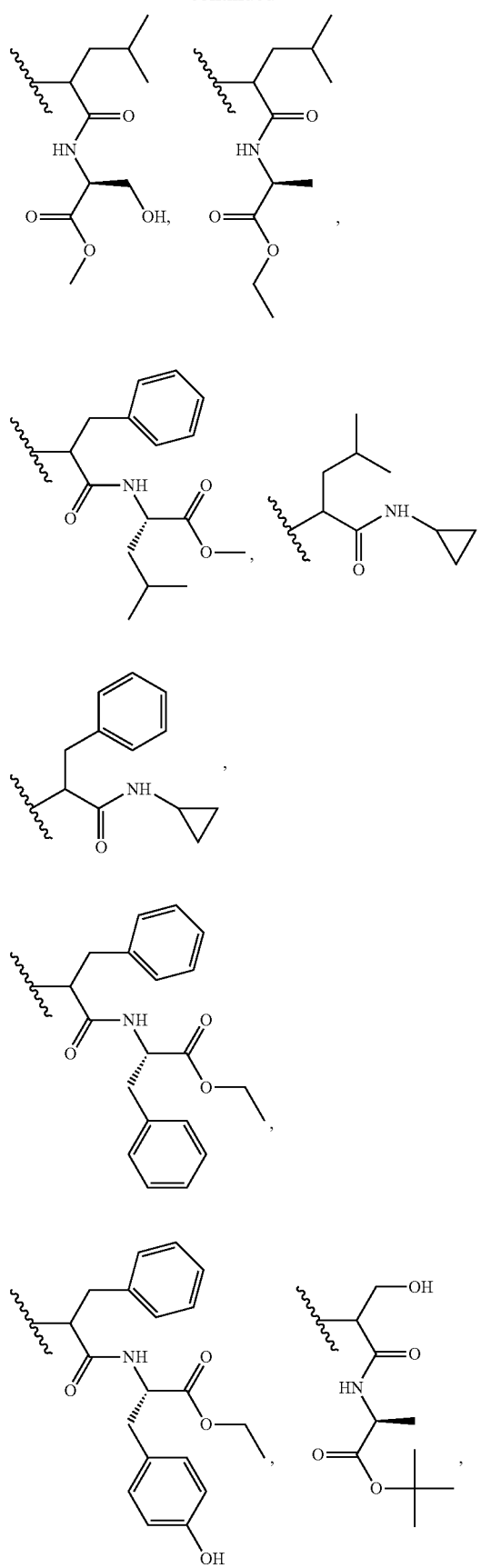
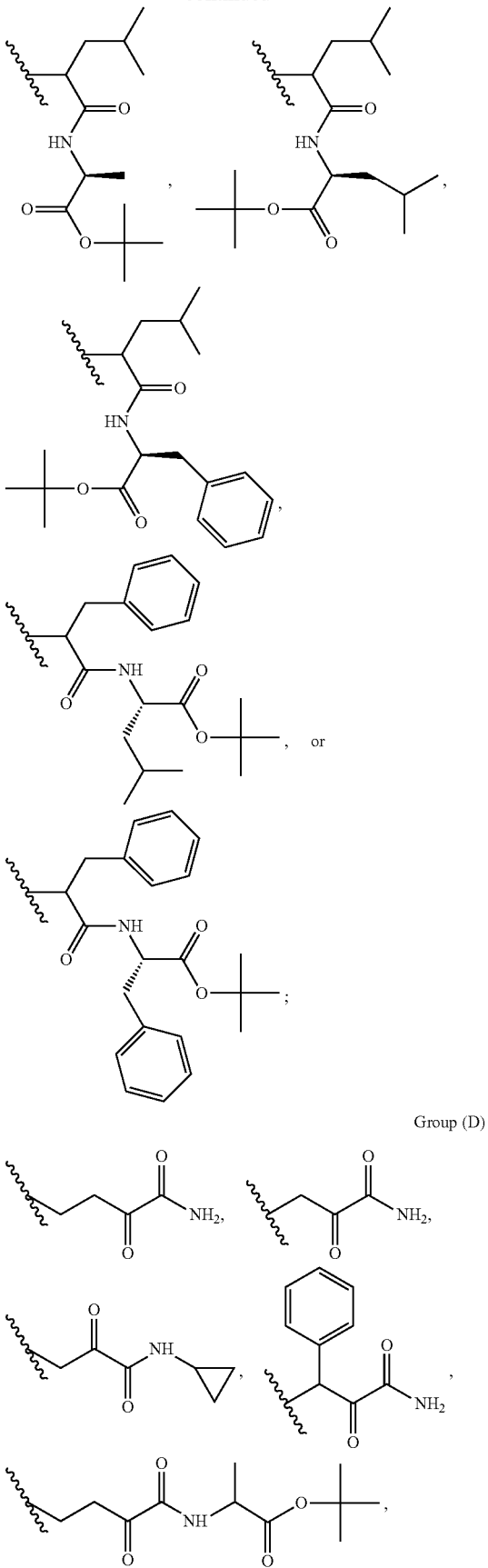

13
-continued
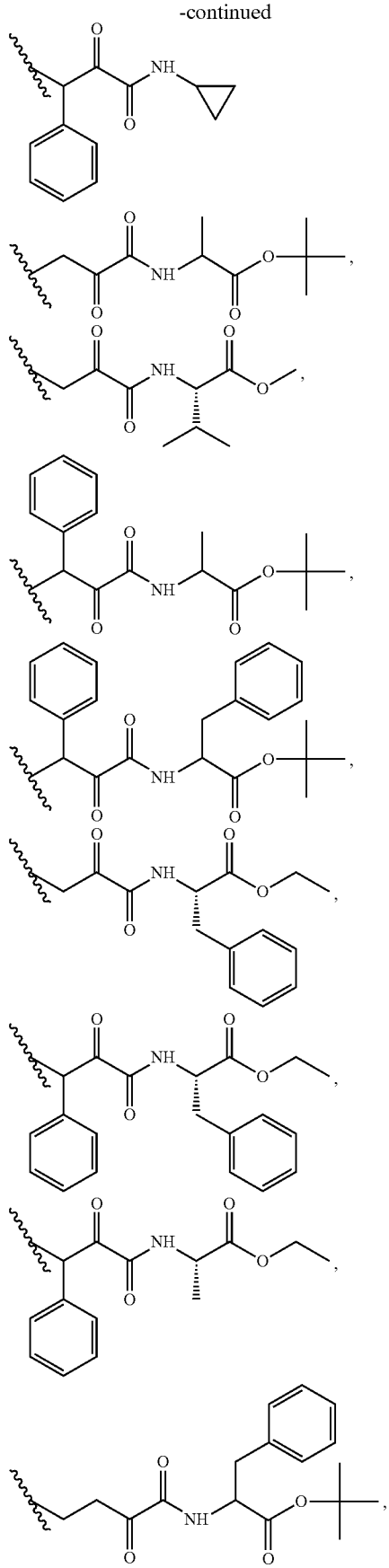
14
-continued
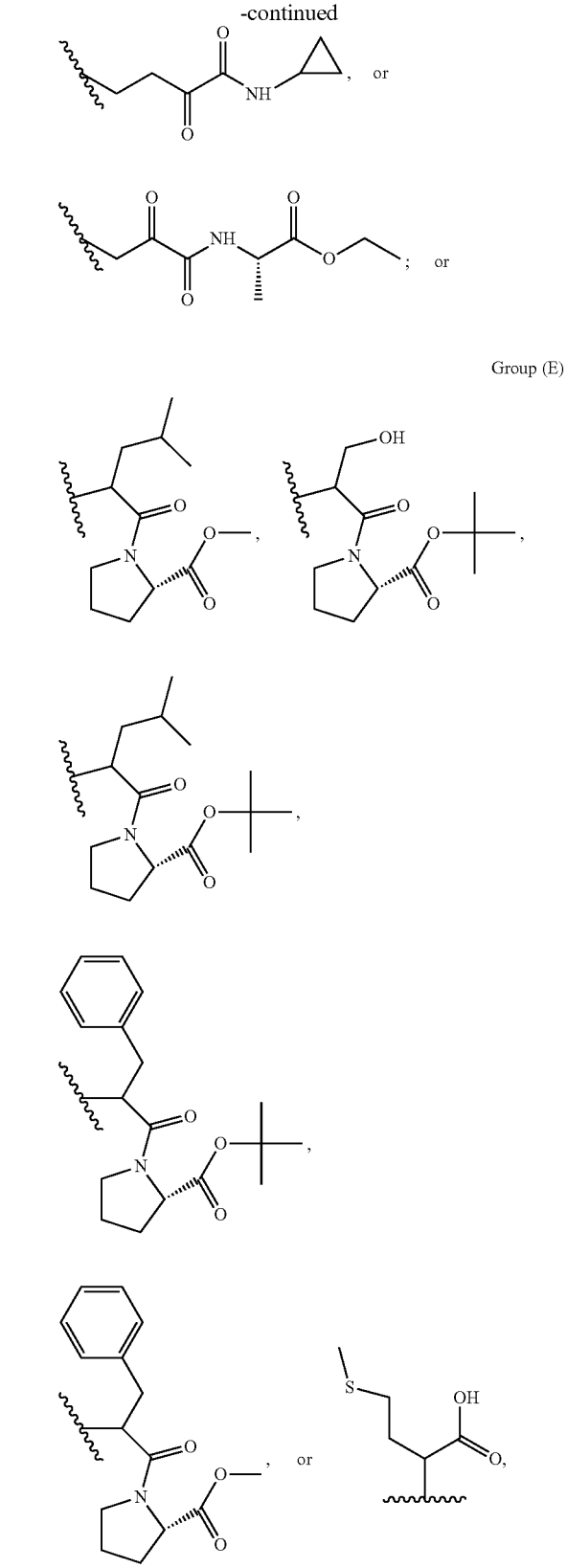
$R_3$ is isobutyl, ～ denotes the place of connection.
More preferably, $R_1$ is H; $R_2$ is selected from the groups as follows:

Group (A)
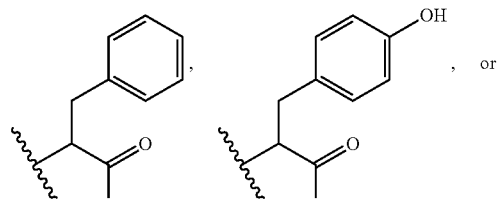
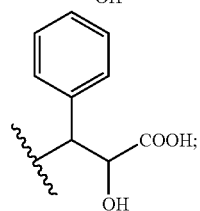
Group (B)
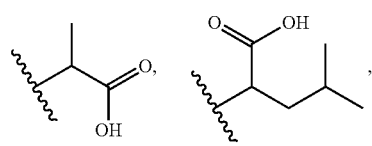
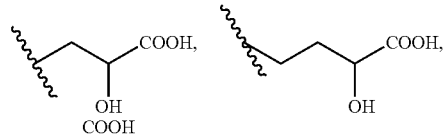
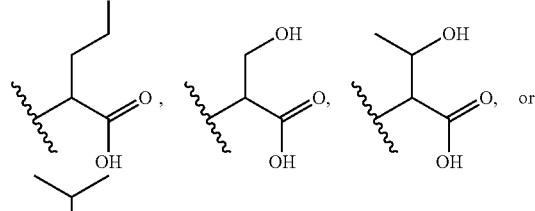
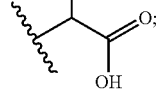
Group (C)
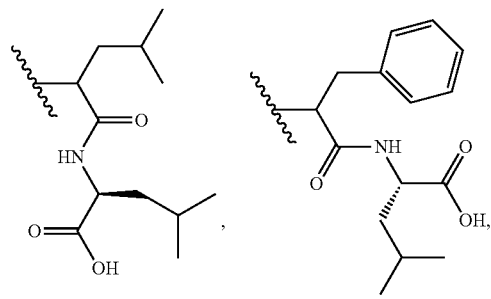
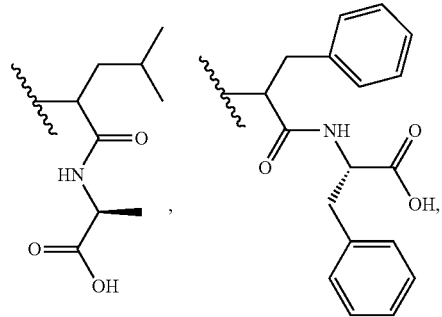
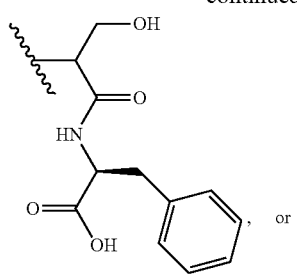
, or
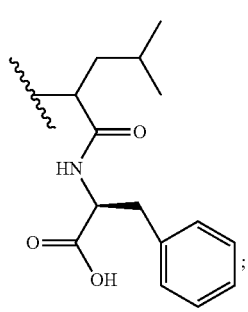
;
Group (D)
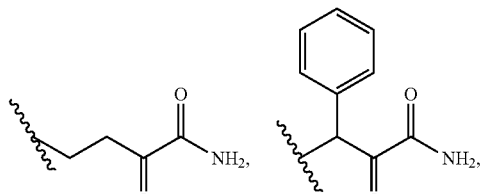
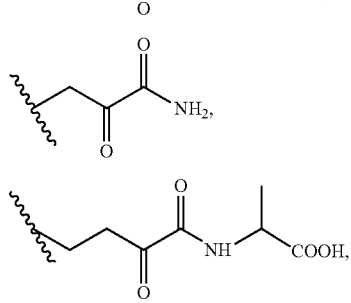
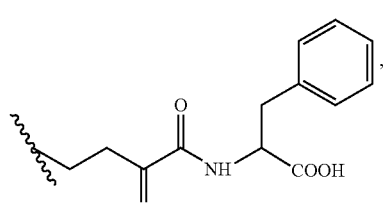
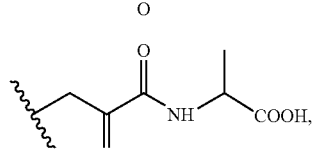
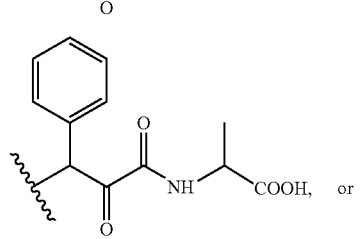, or -continued
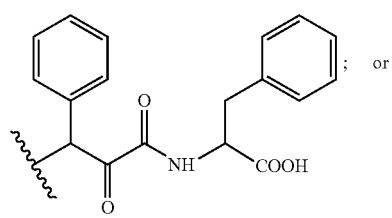; or
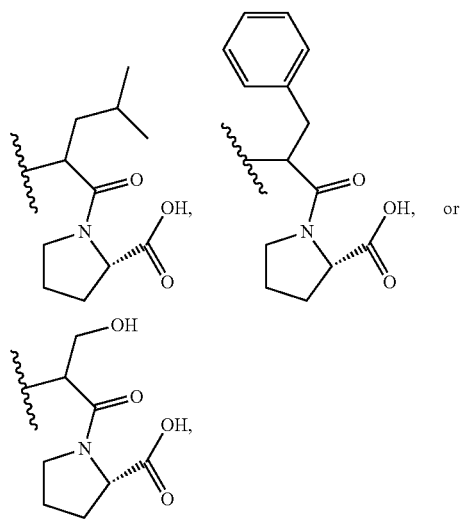
R₃ is isobutyl, ⌇⌇⌇ denotes the place of connection.
The present invention also provides a compound selected from compounds of formula (XIV), pharmaceutically acceptable salts of compounds of formula (XIV), and pharmaceutically acceptable prodrugs of compounds of formula (XIV),
(XIV)
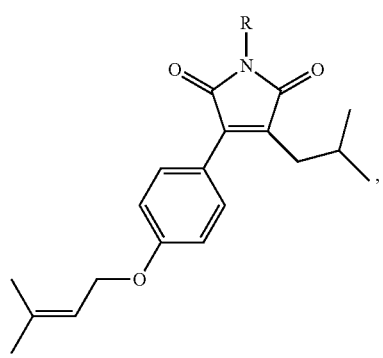
wherein R is
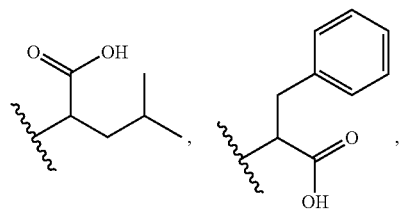
-continued
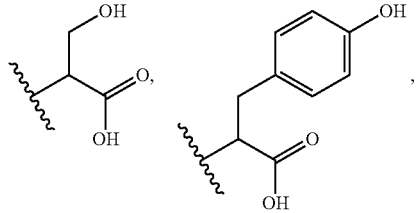
Group (E)
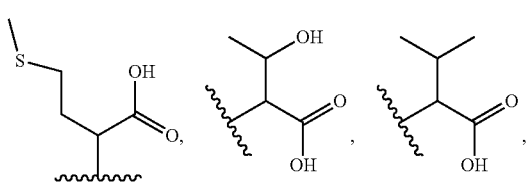
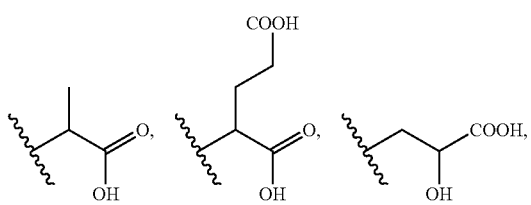
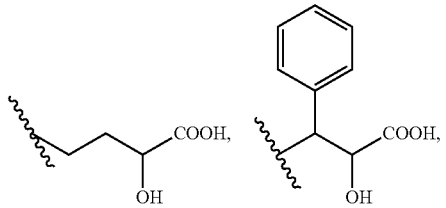
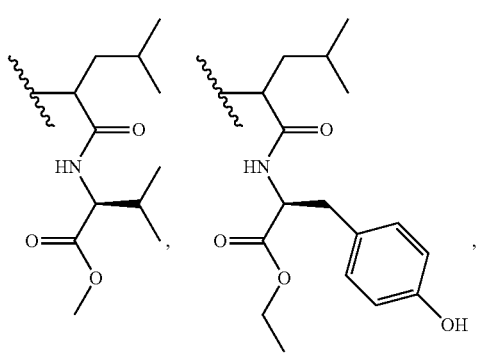
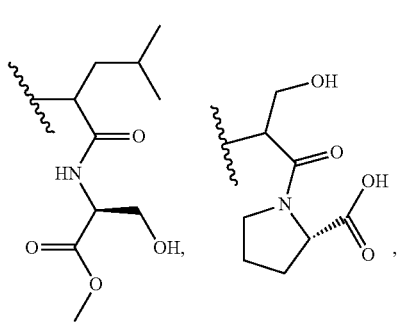

-continued
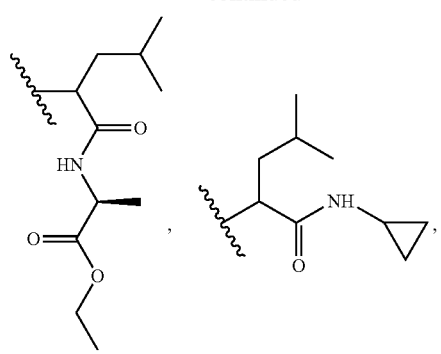
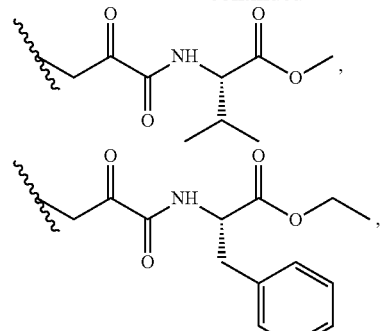
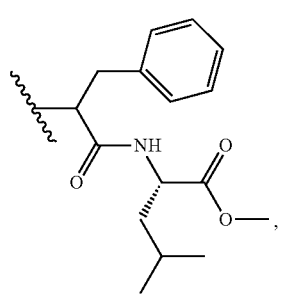
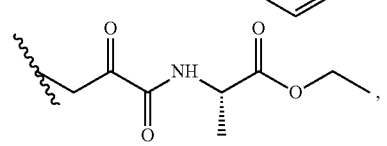
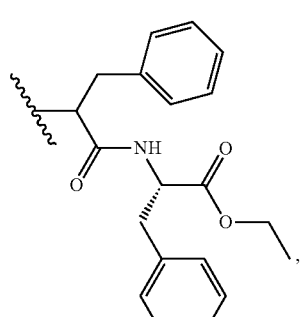
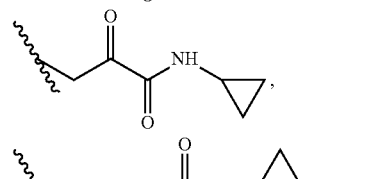
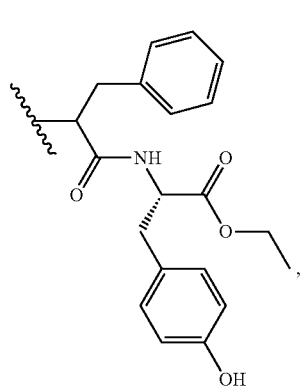
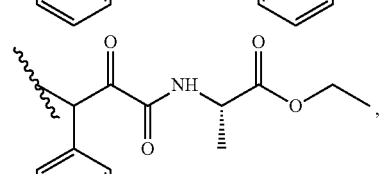
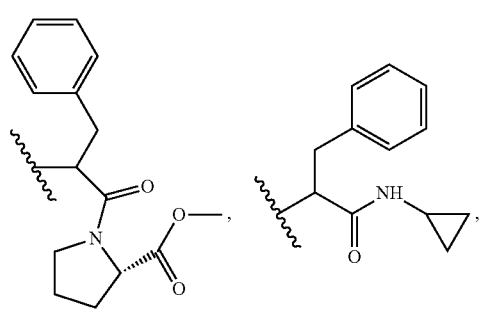
denotes the place of connection.
Preferably, R is
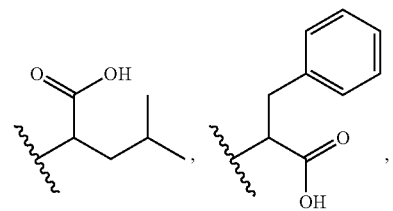

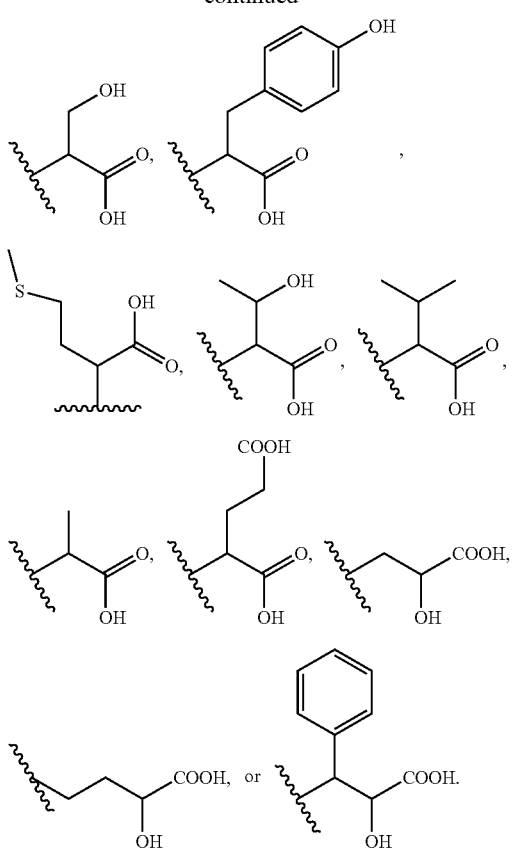

More preferably, R is

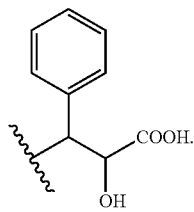 [SMILES: *C(c1ccccc1)C(O)C(=O)O]

The present invention also provides a compound having formula (II),

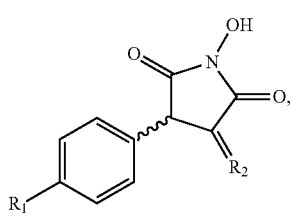
(II)

wherein $R_1$ is $C_{1-10}$ alkyloxy, $C_{2-10}$ alkenyloxy, or $C_{2-10}$ alkynyloxy; and $R_2$ is $C_{1-10}$ alkyl or $C_{2-10}$ alkenyl, or pharmaceutically acceptable salts or prodrugs thereof.

Preferably, the compound is the compound of formula (XIII)

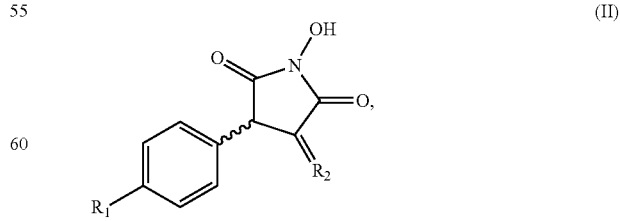
(XIII)

Certain compounds exist in one or more particular geometric, optical, enantiomeric, diasteriomeric, epimeric, stereoisomeric, tautomeric, conformational, or anomeric forms, including but not limited to, (+) and (−) forms; cis- and trans-forms; E- and Z-forms; c-, t-, and r-forms; endo- and exo-forms; R-, S-, and meso-forms; D- and L-forms; d- and l-forms; keto-, enol-, and enolate-forms; syn- and anti-forms; synclinal- and anticlinal-forms; alpha.- and beta.-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

Unless otherwise specified, the compounds of the present invention include all such isomeric forms, including (wholly or partially) racemic and other mixtures thereof. Methods for the preparation (e.g. asymmetric synthesis) and separation (e.g. fractional crystallization and chromatographic means) of such isomeric forms are either known in the art or are readily obtained by adapting the methods taught herein, or known methods, in a known manner.

Unless otherwise specified, the compounds of the present invention also includes ionic, salt, solvate, and protected forms of thereof. It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," J. Pharm. Sci., Vol. 66, pp. 1-19.

The pharmaceutically acceptable salts of the compounds are prepared following procedures which are familiar to those skilled in the art.

The present invention also provides a pharmaceutical composition for treating or prophylaxis of hepatitis C virus (HCV) infection which comprises an effective amount of an active agent selected from
(1) a compound selected from compounds shown in Table 9 or Table 10; or
(2) a compound having the formula (II)

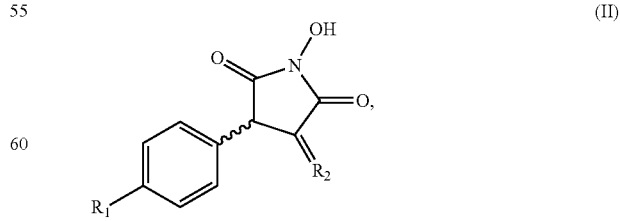
(II)

wherein $R_1$ is $C_{1-10}$ alkyloxy, $C_{2-10}$ alkenyloxy, or $C_{2-10}$ alkynyloxy; and $R_2$ is $C_{1-10}$ alkyl or $C_{2-10}$ alkenyl; and a pharmaceutically acceptable carrier.

Preferably, the compound has formula (XIV)

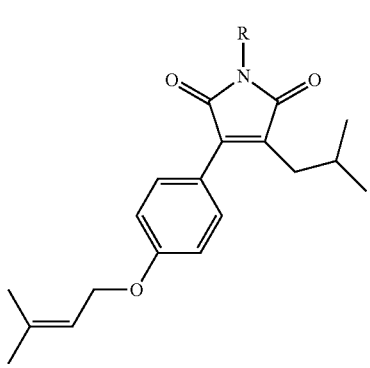

(XIV)

, wherein R is

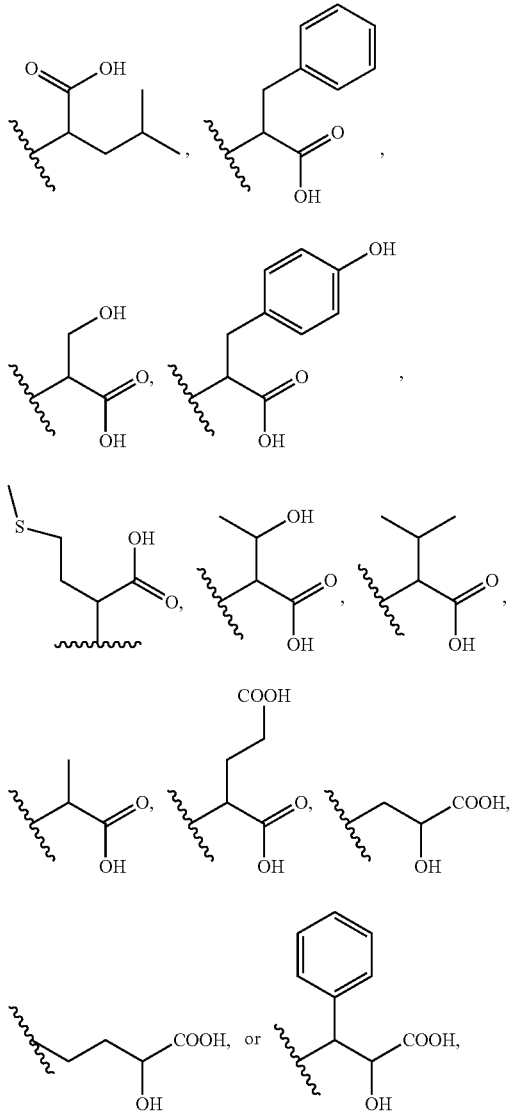

᎔᎔᎔ denotes the place of connection.

More preferably, R is

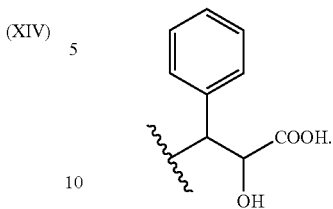

Preferably, the subject is a mammal; more preferably, the subject is a human.

In another preferred embodiment, the compound is a compound of formula (XIII)

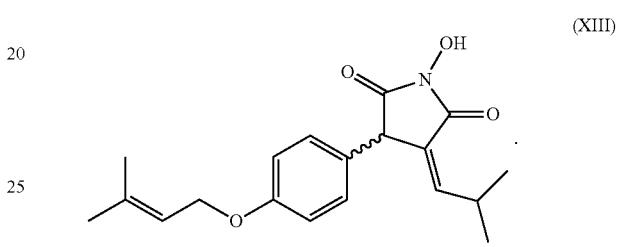

(XIII)

The present invention also provides a pharmaceutical composition for treating or prophylaxis of human immunodeficiency virus (HIV) infection which comprises an effective amount of an active agent selected from
(1) a compound having the formula (II)

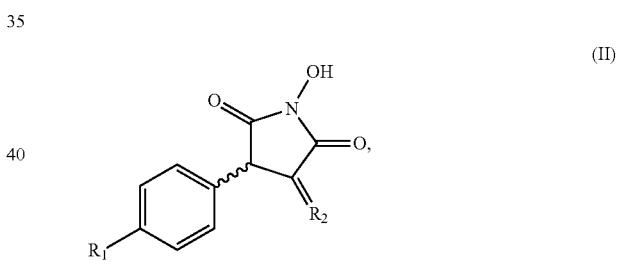

(II)

wherein $R_1$ is $C_{1-10}$ alkyloxy, $C_{2-10}$ alkenyloxy, or $C_{2-10}$ alkynyloxy; and
$R_2$ is $C_{1-10}$ alkyl or $C_{2-10}$ alkenyl; or
(2) a compound having the formula (II)

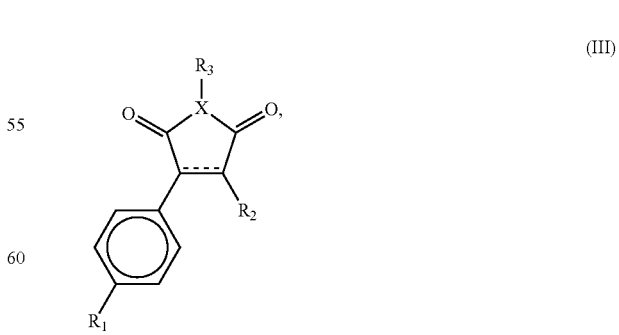

(III)

wherein
- - - denotes a single or double bond;
X is N or O;

$R_1$ is $C_{1-10}$ alkyloxy, $C_{2-10}$ alkenyloxy, or $C_{2-10}$ alkynyloxy;
$R_2$ is H, $C_{1-10}$ alkyl, $C_{2-10}$ alkenyl or $C_{2-10}$ alkynyl; and
$R_3$ is absent, H or hydroxy; provided that if X is O, $R_3$ is absent;
and a pharmaceutically acceptable carrier.

Preferably, the compound is compound of formula (XIII)

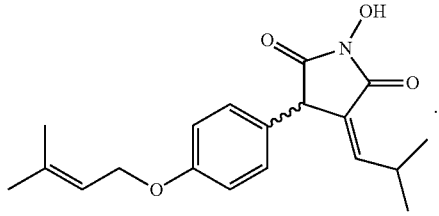

(XIII)

In another preferred embodiment, the compound is
3-isobutyl-4-[4-(3-methyl-2-butenyloxy)phenyl]furan-2,5-dione,
3-isobutyl-4-[4-(3-methyl-2-butenyloxy)phenyl]-1H-pyrrol-2,5-dione,
3-isobutyl-4-[4-(3-methyl-2-butenyloxy)phenyl]-1H-pyrrol-1-ol-2,5-dione,
(3R*,4S*)-1-hydroxy-3-isobutyl-4-[4-(3-methyl-2-butenyloxy)phenyl]pyrrolidine-2,5-dione, or
(3R*,4R*)-1-hydroxy-3-isobutyl-4-[4-(3-methyl-2-butenyloxy)phenyl]-pyrrolidine-2,5-dione.

Preferably, the subject is a mammal; more preferably, the subject is a human.

The composition may be prepared in various forms for administration, including tablets, caplets, pills or dragees, or can be filled in suitable containers, such as capsules, or, in the case of suspensions, filled into bottles. As used herein, "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-viral compounds of the invention, such as by producing any undesirable biological effect or otherwise interacting in a deleterious manner with any other component(s) of the pharmaceutical composition, its use is contemplated to be within the scope of this invention. In the pharmaceutical compositions of the invention, the active agent may be present in an amount of at least 0.5% and not more than 90% by weight based on the total weight of the composition, including carrier medium and/or auxiliary agent(s). Preferably, the proportion of active agent varies between 5%-50% by weight of the composition. Pharmaceutical organic or inorganic solid or liquid carrier media suitable for enteral or parenteral administration can be used to make up the composition. Gelatine, lactose, starch, magnesium, stearate, talc, vegetable and animal fats and oils, gum, polyalkylene glycol, or other known excipients or diluents for medicaments may all be suitable as carrier media.

The present invention further provides a method for treating or prophylaxis of hepatitis C virus (HCV) infection which comprises administering to a subject in need thereof an effective amount of an active agent selected from (1) a compound selected from compounds shown in Table 9 or Table 10;

(2) a compound having the formula (II)

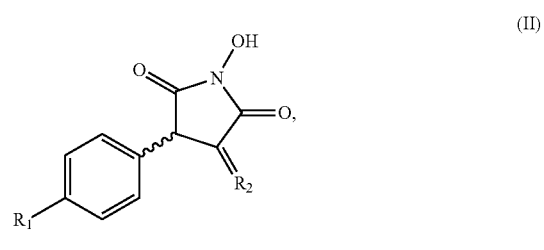

(II)

wherein $R_1$ is $C_{1-10}$ alkyloxy, $C_{2-10}$ alkenyloxy, or $C_{2-10}$ alkynyloxy; and $R_2$ is $C_{1-10}$ alkyl or $C_{2-10}$ alkenyl.

In another preferred embodiment, the compound is a compound of formula (XIII)

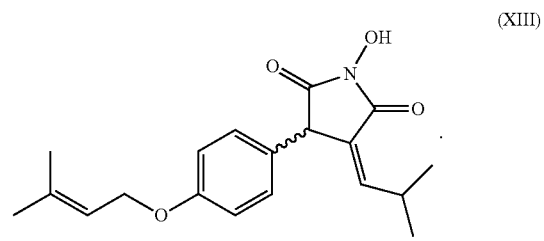 [SMILES: CC(C)=CCOc1ccc(C2C(=O)N(O)C(=O)/C2=C\C(C)C)cc1]

(XIII)

(3) a compound selected from compounds of formula (XIV), pharmaceutically acceptable salts of compounds of formula (XIV), and pharmaceutically acceptable prodrugs of compounds of formula (XIV)

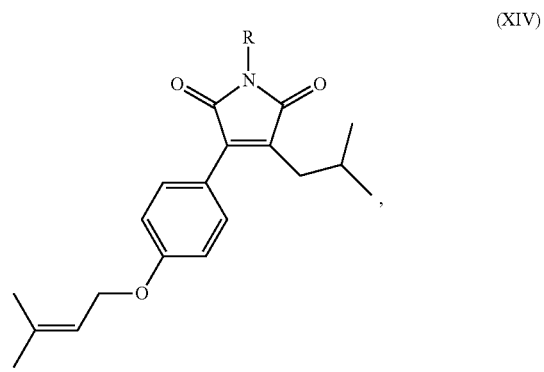

(XIV)

wherein R is

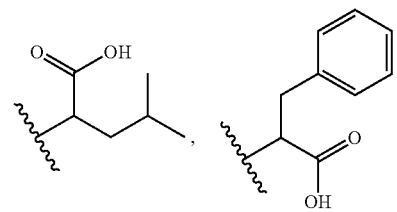

27
-continued
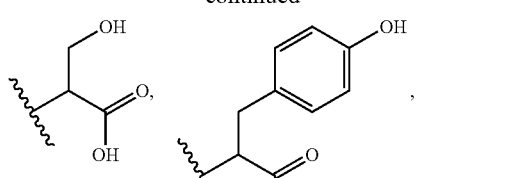
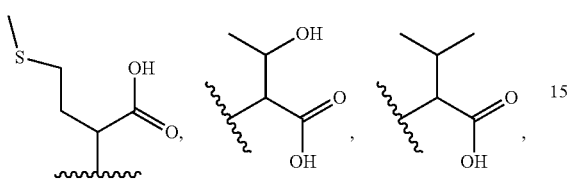
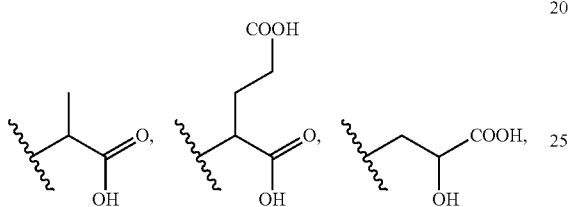
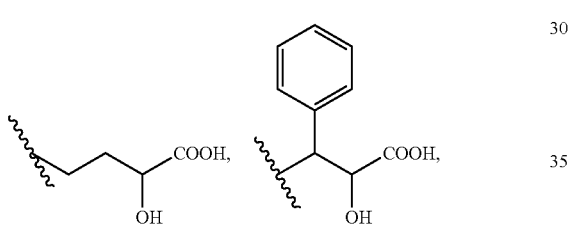
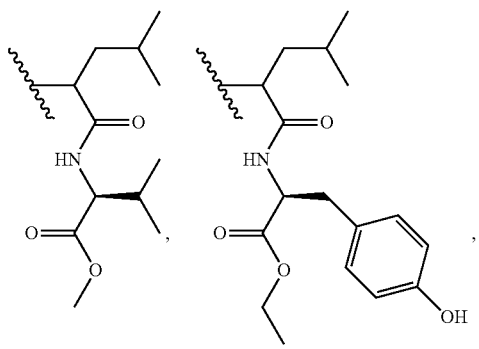
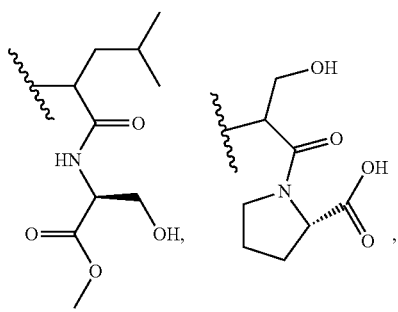
28
-continued
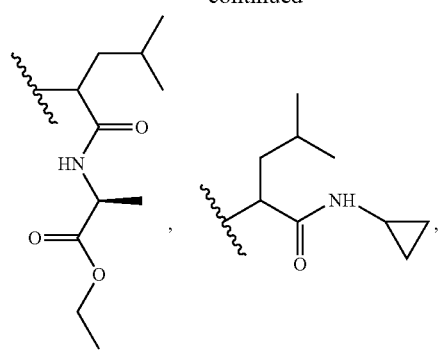
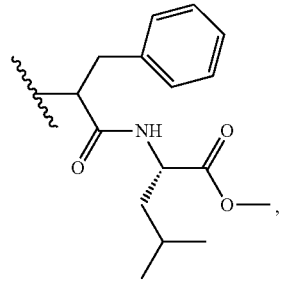
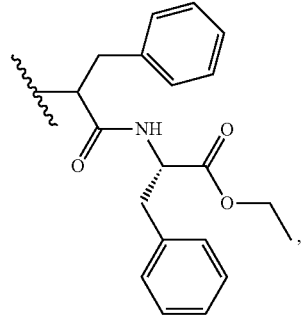
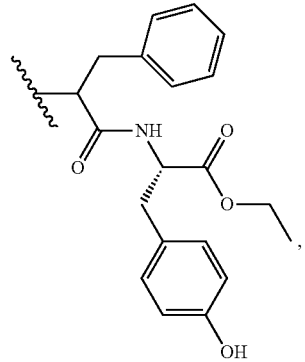
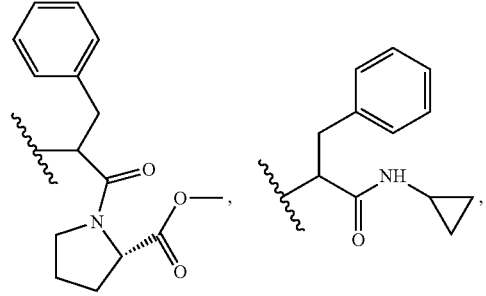

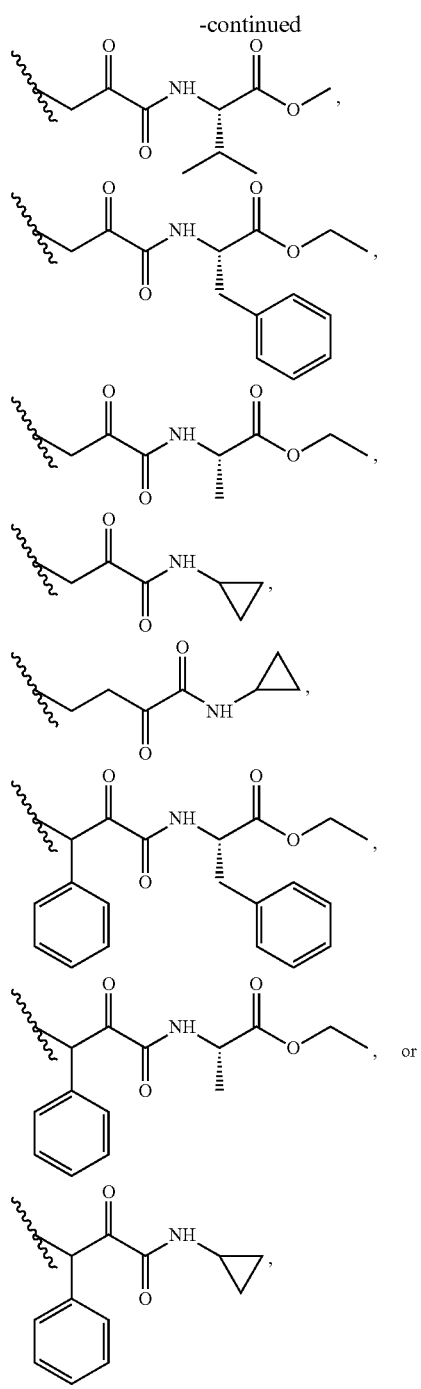

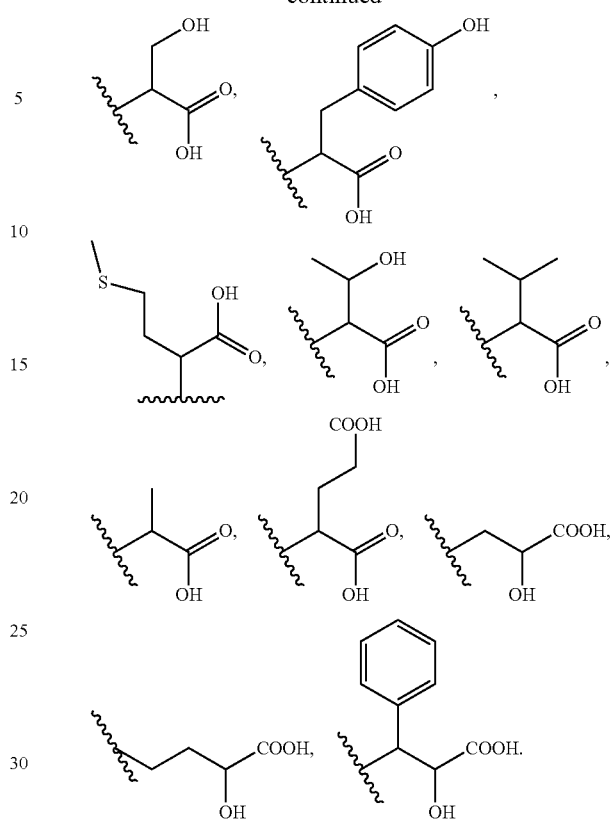

More preferably, R is

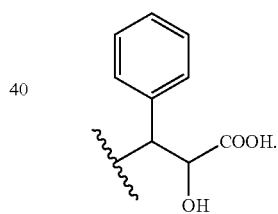

The present invention yet further provides a method for treating or prophylaxis of human immunodeficiency virus (HIV) infection which comprises administering to a subject in need thereof an effective amount of an active agent selected from (1) a compound having the formula (II)

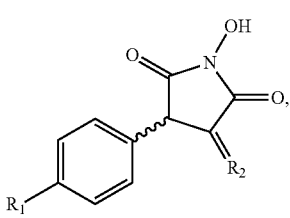

(II)

wherein $R_1$ is $C_{1-10}$ alkyloxy, $C_{2-10}$ alkenyloxy, or $C_{2-10}$ alkynyloxy; and ᨦᨦᨦ denotes the place of connection; or
Preferably, R is

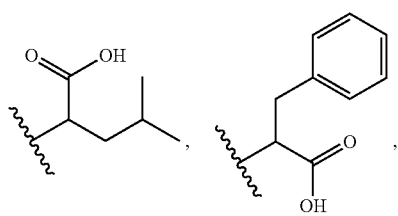

$R_2$ is $C_{1-10}$ alkyl or $C_{2-10}$ alkenyl; or (2) a compound having the formula (III)

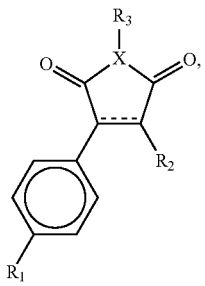

wherein

--- denotes a single or double bond;

X is N or O;

$R_1$ is $C_{1-10}$ alkyloxy, $C_{2-10}$ alkenyloxy, or $C_{2-10}$ alkynyloxy;

$R_2$ is H, $C_{1-10}$ alkyl, $C_{2-10}$ alkenyl or $C_{2-10}$ alkynyl; and $R_3$ is absent, H or hydroxy;

provided that if X is O, $R_3$ is absent.

Preferably, the compound is a compound of formula (XIII)

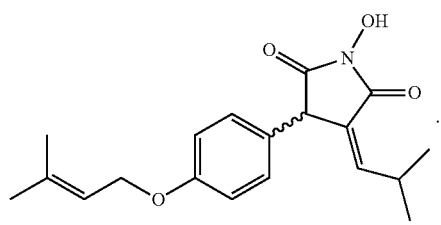

In another preferred embodiment, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, (3R*,4S*)-1-hydroxy-3-isobutyl-4-[4-(3-methyl-2-butenyloxy)phenyl]pyrrolidine-2,5-dione, or (3R*,4R*)-1-hydroxy-3-isobutyl-4-[4-(3-methyl-2-butenyloxy)phenyl]pyrrolidine-2,5-dione.

The compounds of the invention may be administered using any amount and any route of administration effective for attenuating infectivity of the hepatitis C virus or the human immunodeficiency virus. Thus, the term "effective amount" used herein refers to a nontoxic but sufficient amount of the antiviral agent to provide the desired treatment of viral infection. The exact amount required will vary from subject to subject, depending on the species, age, and general condition of the subject, the severity of the infection, the particular antiviral agent and its mode of administration, and the like. The compounds are preferably formulated in dosage unit form for ease of administration and uniformity of dosage. Dosage unit form as used herein refers to a physically discrete unit of anti-viral agent appropriate for the patient to be treated. Each dosage should contain the quantity of active material calculated to produce the desired therapeutic effect either as such, or in association with the selected pharmaceutical carrier medium.

The compounds of the invention may be administered orally, parenterally, such as by intramuscular injection, intraperitoneal injection, intravenous infusion or the like, depending on the severity of the infection being treated.

Although the compounds of the present invention can be administered to any patient who is susceptible to hepatitis C virus infection or human immunodeficiency virus infection, the compounds are intended for the treatment of mammalian hosts, and especially humans.

In view of the inhibitory effect on enzyme activity produced by the compounds of the invention, it is anticipated that these compounds will be useful not only for therapeutic treatment of infection, but for prophylaxis, as well. The above-noted dosages will be essentially the same whether for treatment or prophylaxis of hepatitis C virus infection or human immunodeficiency virus.

The following examples are provided to describe the invention in further detail. These examples, which set forth the best mode presently contemplated for carrying out the invention, are intended to illustrate and not to limit the invention.

EXAMPLE

The examples below are non-limiting and are merely representative of various aspects and features of the present invention.

Example 1

General Methods for the Preparation of Compounds of the Present Invention

Apparatus:

NMR spectra were obtained on a Varian Unity Plus 500 $^1$H, 500 MHz; $^{13}$C, 125 MHz) spectrometer. MS spectrum was measured on an electrospray ionization mass spectrometer (ESI-MS, Esquire 3000$^{Plus}$, Bruker Daltonik GmbH, Bremen, Germany).

(1) General Method for the Preparation of Derivatives A1~A9, KA, KB and KC

To 0.01 mol of a compound of formula (IV) in dehydrated DMF (2 mL), 0.011 mol of the corresponding amino acid was added and the mixture was refluxed for 10 min. at 140° C. The reaction was stopped by adding 5 mL water and extracted with ethyl acetate (3×5 mL). The pooled ethyl acetate fractions were washed with brine (1×5 mL), dried over MgSO$_4$ and evaporated under vacuum. The residue was purified using silica gel column CHCl$_3$:MeOH 9.5/0.5 v/v.

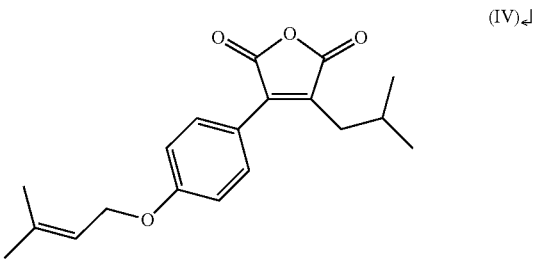 [SMILES: CC(C)=CCOc1ccc(C2=C(CC(C)C)C(=O)OC2=O)cc1]

2-(3-Isobutyl-4-(4-(3-methylbut-2-enyloxy)phenyl)-2,5-dioxo-2,5-dihydro-H-pyrrol-1-yl)-4-methylpentanoic acid. (A1)

Obtained as yellow oil, $^1$H NMR (CDCl$_3$, 400 MHz) δ 0.89 (d, J=6.8 Hz, 6H), 0.94 (d, J=6.4 Hz, 6H), 1.75 (s, 3H), 1.80 (s, 3H), 1.90 (m, 1H), 2.06 (m, 1H), 2.3 (m, 1H), 2.52 (d, J=7.2 Hz, 2H), 4.80 (dd, J=4, 11.6 Hz, 1H), 4.55 (d, J=7.2 Hz, 2H), 5.49 (m, 1H), 6.97 (d, J=8.4 Hz, 2H), 7.53 (d, J=8.4 Hz, 2H); $^{13}$C NMR (CDCl$_3$, 100 MHz) δ 18.1, 20.9, 22.6, 22.6, 23.1, 25.2, 25.8, 28.0, 31.6, 32.8, 36.7, 37.1, 50.7, 64.8, 114.6, 119.2, 121.3, 130.9, 137.5, 138.1, 138.5, 159.8, 163.2, 170.8, 171.6, 173.4. ESI-MS m/z 428 [M+H]$^+$.

2-(3-Isobutyl-4-(4-(3-methylbut-2-enyloxy)phenyl)-2,5-dioxo-2,5-dihydro-H-pyrrol-1-yl)-3-phenylpropanoic acid (A2)

Obtained as yellow oil. $^1$H NMR (CDCl$_3$, 400 MHz) δ 0.78 (d, J=6.4 Hz, 6H), 0.76 (d, J=6.4 Hz, 6H), 1.76 (s, 3H), 1.80 (s, 3H), 1.9 (m, 1H), 2.40 (d, J=7.2 Hz, 2H), 3.50 (m, 2H), 4.52 (d, J=6.8 Hz, 2H), 5.06 (t. J=7.2, 16.4 Hz, 1H), 5.49 (m, 1H), 6.93 (d, J=8.4 Hz, 2H), 7.15 (m, 3H), 7.22 (d, J=6.8 Hz, 2H), 7.39 (d, J=8.4 Hz, 2H). $^{13}$C NMR (CDCl$_3$, 100 MHz) δ18.2, 22.5, 22.6, 25.8, 27.9, 32.7, 34.4, 53.0, 64.8, 114.7, 119.2, 121.1, 126.8, 128.5, 128.9, 130.8, 136.6, 137.5, 138.0, 138.6, 159.9, 170.3, 171.1, 174.0. ESI-MS m/462 [M+H]$^+$.

3-Hydroxy-2-(3-Isobutyl-4-(4-(3-methylbut-2-enyloxy)phenyl)-2,5-dioxo-2,5-dihydro-1H-pyrrol-1-yl) propanoic acid (A3)

Obtained as yellow oil. $^1$H NMR (CDCl$_3$, 400 MHz) δ 0.89 (d, J=6.4 Hz, 6H), 1.75 (s, 3H), 1.81 (s, 3H), 2.04 (m, 1H), 2.54 (d, J=8 Hz, 2H), 4.12 (dd, J=3.6, 8.4 Hz, 1H), 4.23 (dd, J=5.2, 12 Hz, 1H), 4.56 (d, J=6.8 Hz, 2H), 4.90 (m, 1H), 5.49 (t, J=6.8, 13.6 Hz, 1H), 6.96 (d, J=8.6 Hz, 2H), 7.50 (d, J=8.8 Hz, 2H). $^{13}$C NMR (CDCl$_3$, 100 MHz) δ18.2, 22.7, 25.8, 27.9, 28.1, 32.9, 33.6, 54.9, 61.1, 64.8, 64.9, 114.8, 115.1, 118.8, 119.1, 120.9, 130.9, 131.1, 138.2, 138.6, 138.7, 160.0, 171.0, 171.3, 172.1. ESI-MS m/z 402 [M+H]$^+$.

3-(4-Hydroxyphenyl)-2-(3-Isobutyl-4-(4-(3-methylbut-2-enyloxy)-phenyl)-2,5-dioxo-2,5-dihydro-1H-pyrrol-1-yl)propanoic acid (A4)

Obtained as yellow oil. $^1$H NMR (CDCl$_3$, 400 MHz) δ δ 0.78 (d, J=6.8 Hz, 3H), 0.80 (d, J=6.8 Hz, 3H), 1.75 (s, 1H), 1.80 (s, 1H), 1.92 (m, 1H), 2.41 (d, J=7.2 Hz, 2H), 3.43 (d, J=12.8 Hz, 2H), 4.53 (d, J=6.8 Hz, 2H), 5.00 (t, J=8.4, 17.2 Hz, 1H), 5.48 (t, J=6.8, 13.6 Hz, 1H), 6.67 (d, J=8.4 Hz, 2H), 6.94 (d, J=9.2 Hz, 2H), 7.00 (d, J=9.2 Hz, 2H), 7.40 (d, J=8.4 Hz, 2H); $^{13}$C NMR (CDCl$_3$, 100 MHz) δ 18.2, 22.5, 22.6, 25.8, 28.0, 32.7, 33.6, 53.1, 64.8, 71.1, 114.7, 115.4, 119.2, 121.1, 128.6, 130.1, 130.9, 137.6, 138.1, 138.7, 154.4, 159.9, 170.4, 171.2, 173.7. ESI-MS m/z 478 [M+H]$^+$.

2-(3-Isobutyl-4-(3-methylbut-2-enyloxy)phenyl)-2,5-dioxo-2,5-dihydro-1H-pyrrol-1-yl)-4-(methylthio) butanoic acid (A5)

Obtained as yellow oil. $^1$H NMR (CDCl$_3$, 400 MHz) δ 0.89 (d, J=6.8 Hz, 6H), 1.75 (s, 1H), 1.81 (s, 1H), 2.03 (m, 1H), 2.05 (s, 3H), 2.45 (m, 4H), 2.50 (d, J=8 Hz, 2H), 4.53 (d, J=7.4 Hz, 2H), 5.00 (m, 1H), 5.49 (t, J=7.2, 16.4 Hz, 1H), 6.97 (d, J=8.8 Hz, 2H), 7.53 (d, J=8.8 Hz, 2H); $^{13}$C NMR (CDCl$_3$, 100 MHz) δ 15.3, 18.2, 22.7, 25.8, 27.7, 28.1, 30.9, 32.9, 50.7, 64.8, 114.7, 119.1, 121.1, 130.9, 137.9, 138.3, 138.7, 159.9, 170.6, 171.4, 174.7. ESI-MS m/z 446 [M+H]$^+$.

3-Hydroxy-2-(3-isobutyl-4-(4-(3-methylbut-2-enyloxy)phenyl)-2,5-dioxo-2,5-dihydro-1H-pyrrol-1-yl) butanoic acid (A6)

Obtained as yellow oil. $^1$H NMR (CDCl$_3$, 400 MHz) δ 0.89 (d, J=6.8 Hz, 6H), 1.21 (d, J=6.4 Hz, 3H), 1.76 (s, 3H), 1.81 (s, 3H), 2.06 (m, 1H), 2.55 (d, J=7.6 Hz, 2H), 4.55 (d, J=6.4 Hz, 2H), 4.67 (dd, J=4, 6.4 Hz, 1H), 4.88 (d, J=4 Hz, 1H), 5.49 (t, J=5.2, 13.2 Hz, 1H), 6.99 (d, J=8.4 Hz, 2H), 7.54 (d, J=8.4 Hz, 2H); $^{13}$C NMR (CDCl$_3$, 100 MHz) δ 18.2, 20.1, 22.7, 25.8, 28.2, 32.9, 59.2, 64.9, 66.7, 114.8, 119.1, 120.8, 131.1, 138.4, 138.7, 160.2, 170.5, 171.8, 172.8. ESI-MS m/z 416 [M+H]$^+$.

2-(3-Isobutyl-4-(4-(3-methylbut-2-enyloxy)phenyl)-2,5-dioxo-2,5-dihydro-1H-pyrrol-1-yl)-3-methylbutanoic acid (A7)

Obtained as yellow oil. $^1$H NMR (CDCl$_3$, 400 MHz) δ 0.89 (d, J=6.4 Hz, 6H), 0.92 (d, J=6.4 Hz, 3H), 1.12 (d, J=6.4 Hz, 3H), 1.76 (s, 3H), 1.80 (s, 3H), 2.04 (m, 1H), 2.45 (m, 1H), 2.53 (d, J=7.2 Hz, 2H), 2.67 (m, 1H), 4.48 (d, J=8.0 Hz, 1H), 4.55 (d, J=−6.8 Hz, 1H), 5.48 (t, J=7.2, 16.4 Hz, 1H), 6.97 (d, J=8.4 Hz, 2H), 7.54 (d, J=8.4 Hz, 2H); $^{13}$C NMR (CDCl$_3$, 100 MHz) δ 18.2, 19.4, 20.7, 22.7, 25.8, 28.1, 28.4, 32.9, 57.8, 64.9, 114.8, 119.2, 121.2, 131.0, 137.6, 138.1, 138.7, 160.0, 170.8, 171.6, 173.6. ESI-MS m/z 414 [M+H]$^+$.

2-(3-Isobutyl-4-(4-(3-methylbut-2-enyloxy)phenyl)-2,5-dioxo-2,5-dihydro-1H-pyrrol-1-yl) propanoic acid (A8)

Obtained as yellow oil. $^1$H NMR (CDCl$_3$, 400 MHz) δ 0.89 (d, J=6.4 Hz, 6H), 1.66 (d, J=7.2 Hz, 3H), 1.76 (s, 3H), 1.81 (s, 3H), 2.05 (m, 1H), 2.51 (d, J=7.2 Hz, 2H), 4.55 (d, J=6.8 Hz, 2H), 4.85 (m, 1H), 5.49 (m, 1H), 6.97 (d. J=8.4 Hz, 2H), 7.52 (d, J=8.4 Hz, 2H); $^{13}$C NMR (CDCl$_3$, 100 MHz) δ 15.2, 18.2, 22.7, 25.8, 28.1, 32.9, 47.4, 64.8, 114.7, 119.2, 121.3, 131.0, 137.8, 138.3, 138.6, 159.9, 170.3, 171.3, 173.7; ESI-MS m/z 386 [M+H]$^+$.

2-(3-Isobutyl-4-(3-methylbut-2-enyloxy)phenyl)-2,5-dioxo-2-dihydro-1H-pyrrol-1-yl)pentanedioic acid (A9)

Obtained as yellow oil. $^1$H NMR (CDCl$_3$, 400 MHz) δ 0.88 (d, J=6.8 Hz, 6H), 1.75 (s, 3H), 1.80 (s, 3H), 2.04 (m, 1H), 2.43 (br s, 4H), 2.52 (d, J=7.2 Hz, 2H), 4.55 (d, 6.8 Hz, 2H), 4.84 (dd, J=5.2, 9.2 Hz, 1H), 5.49 (t, J=7.2, 16.4 Hz, 1H), 6.96 (d, J=8.8 Hz, 2H), 7.51 (d, J=8.8 Hz, 2H); $^{13}$C NMR (CDCl$_3$, 100 MHz) δ 18.2, 22.7, 23.8, 25.8, 28.1, 30.5, 32.9, 50.9, 64.9, 114.8, 119.2, 121.1, 131.0, 137.9, 138.4, 138.7, 160.0, 170.6, 171.4, 174.3, 177.9; ESI-MS m/z 444 [M+H].

2-Hydroxy-3-(3-isobutyl-4-(4-(3-methylbut-2-enyloxy)phenyl)-2,5-dioxo-2,5-dihydro-1H-pyrrol-1-yl) propanoic acid (KA)

Obtained as yellow oil. $^1$H NMR (CDCl$_3$, 400 MHz) δ 0.87 (d, J=7.2 Hz, 6H), 1.75 (s, 3H), 1.81 (s, 3H), 1.99 (m, 1H), 2.51 (d, J=7.2 Hz, 2H), 3.82 (m, 2H), 4.39 (dd, J=6, 7.2 Hz, 1H), 5.49 (t, J=7.2, 16.4 Hz, 1H), 6.98 (d. J=8.8 Hz, 2H), 7.49 (d, J=8.8 Hz, 2H); $^{13}$C NMR (CDCl$_3$, 100 MHz) δ 18.2, 22.8, 25.9, 28.2, 32.9, 33.9, 64.9, 114.8, 119.1, 121.0, 130.9, 138.0, 138.2, 138.8, 145.1, 151.1, 160.1, 170.6, 171.9, 172.7; ESI-MS m/z 402 [M+H]$^+$.

2-Hydroxy-4-(3-isobutyl-4-(4-(3-methylbut-2-enyloxy)phenyl)-2,5-dioxo-2,5-dihydro-1H-pyrrol-1-yl) butanoic acid (KB)

Obtained as yellow oil. $^1$H NMR (CDCl$_3$, 400 MHz) δ 0.89 (d, J-6.4 Hz, 6H), 1.75 (s, 3H), 1.81 (s, 3H), 2.02 (m, 1H), 2.20

(br s, 1H), 2.51 (d, J=7.6 Hz, 2H), 3.75 (m, 2H), 4.18 (br s, 1H), 4.55 (d, J=6.8 Hz, 2H), 5.49 (t, J=7.2, 16.4 Hz, 1H), 6.98 (d, J=8.8 Hz, 2H), 7.49 (d, J=–8.8 Hz, 2H); $^{13}$C NMR (CDCl$_3$, 100 MHz) δ 18.2, 22.8, 25.9, 28.2, 32.9, 33.9, 64.9, 114.8, 119.1, 121.0, 130.9, 138.0, 138.2, 138.8, 145.1, 151.1, 160.1, 170.6, 171.9, 172.7: ESI-MS m/z 416 [M+H]$^+$.

2-Hydroxy-3-(3-isobutyl-4-(4-(3-methylbut-2-enyloxy)phenyl)-2,5-dioxo-2,5-dihydro-1H-pyrrol-1-yl)-3-phenylpropanoic acid (KC)

Obtained as yellow oil. $^1$H NMR (CDCl$_3$, 400 MHz) δ 0.88 (d, J=6.8 Hz, 6H), 1.75 (s, 3H), 1.81 (s, 3H), 2.03 (m, 1H), 2.53 (d, J=7.2 Hz, 2H), 4.55 (d, 6.8 Hz, 2H), 4.98 (d, J=4.8 Hz, 1H), 5.49 (t, J=6.4, 15.2 Hz, 1H), 5.85 (d, J=4.8 Hz, 1H), 6.97 (d, J=8.4 Hz, 2H), 7.32 (m, 5H), 7.51 (d, J=8.4 Hz, 2H); $^{13}$C NMR (CDCl$_3$, 100 MHz) δ 18.2, 22.7, 25.8, 28.2, 32.9, 57.0, 64.9, 114.8, 115.1, 119.1, 120.7, 127.4, 128.3, 128.9, 131.1, 135.5, 138.1, 138.4, 138.8, 160.3, 171.7, 172.9, 173.1; ESI-MS m/z 478 [M+H]$^+$.

(2) General Method for the Preparation of Compounds A1-1~A1-6 and A2-1~A2~5

A mixture of respective carboxylic acid derivative (A1-A9) (31 mmol), amino acid ester derivative (34.9 mmol) and L-hydroxybenzotriazole hydrate (38.5 mmol) were dissolved in dimethylformamide (60 mL). The resulting solution was then placed in a water bath at 0° C. and treated with triethylamine (14 mL), followed by stirring for 10 min. To the resulting mixture 1-(3-(dimethyl-amino)propyl)-3-ethylcarbodiimide hydrochloride (38.5 mmol) was added. After removing the water bath, the mixture was stirred for 18 h at room temperature. The reaction was diluted in water (200 mL), extracted with ethyl acetate, dried over sodium sulfate anhydrous, concentrated under reduced pressure and purified by silica gel column chromatography, eluting by hexane:ethyl acetate 9:1 v/v.

Methyl 2-(2-(3-isobutyl-4-(4-(3-methylbut-2-enyloxy)phenyl)-2,5-dioxo-2,5-dihydro-1H-pyrrol-1-yl)-4-methylpentanamido)-3-methyl-butanoate (A1-1)

Obtained as yellow oil. $^1$H NMR (CDCl$_3$, 400 MHz) δ 0.87 (d. J=6.4 Hz, 6H), 0.94 (d, J=6.4 Hz, 6H), 1.45 (m, 1H), 1.76 (s, 3H), 1.81 (s, 3H), 1.87 (m, 1H), 2.06 (m, 1H), 2.17 (m, 1H), 2.90 (m, 1H), 2.54 (d, J=7.2 Hz, 2H), 3.72 (s, 3H), 4.54 (d, J=8 Hz, 1H), 4.55 (d. J=6.8 Hz, 2H), 4.80 (dd, J=4.8, 10.8 Hz, 1H), 5.49 (m, 1H), 6.98 (d, J=8.8 Hz, 2H), 7.53 (d, J=8.8 Hz, 2H); $^{13}$C NMR (CDCl$_3$, 100 MHz) δ 17.7, 18.2, 18.9, 21.3, 22.7, 23.0, 25.3, 25.8, 28.1, 31.3, 32.8, 37.6, 52.1, 53.6, 57.2, 64.8, 114.8, 119.1, 121.1, 130.9, 137.8, 138.2, 138.7, 160.0, 169.6, 171.1, 172.0, 172.1. ESI-MS m/z 541 [M+H]$^+$.

Ethyl 3-(4-hydroxyphenyl)-2-(2-(3-isobutyl-4-(4-(3-methylbut-2-enyloxy)phenyl)-2,5-dioxo-2,5-dihydro-1H-1-yl)-4-methylpentanamido)propanoate (A1-2)

Obtained as yellow oil. $^1$H NMR (CDCl$_3$, 400 MHz) δ 0.88 (d, J=6.8 Hz, 9H), 0.9 (d, J=6.8 Hz, 3H), 1.28 (t, J=7.2, 14.4 Hz, 3H), 1.39 (m, 1H), 1.76 (s, 3H), 1.81 (s, 3H), 2.03 (m, 1H), 2.33 (m, 1H), 2.51 (d, J=8 Hz, 2H), 2.98 (dd, J=6.4, 14.4 Hz, 1H), 3.07 (dd, 6.6, 14 Hz, 1H), 4.15 (m, 2H), 4.55 (d, J=6.4 Hz, 2H), 4.75 (m, 2H), 5.49 (m, 1H), 6.66 (d, J=8.8 Hz, 2H), 6.93 (d, J=8.8 Hz, 2H), 6.98 (d, J=8.8 Hz, 2H), 7.51 (d, J=8.8 Hz, 2H); $^{13}$C NMR (CDCl$_3$, 100 MHz) δ 14.1, 18.2, 21.4, 22.7, 22.9, 25.3, 25.8, 28.1, 32.8, 37.1, 37.3, 53.3, 53.6, 61.6, 64.9, 114.8, 115.4, 119.1, 121.1, 127.3, 130.4, 131.0, 137.7, 138.2, 138.7, 154.9, 160.0, 169.4, 171.1, 171.4, 171.9. ESI-MS m/z 619 [M+H]$^+$.

Methyl 3-hydroxy-2-(2-(3-Isobutyl-4-(4-(3-methylbut-2-enyloxy)-phenyl)-2,5-dioxo-2,5-dihydro-1H-pyrrol-1-yl)-4-methylpentanamido)-propanoate (A1-3)

Obtained as yellow oil. $^1$H NMR (CDCl$_3$, 400 MHz) δ 0.89 (d, J=6.8 Hz, 6H), 0.93 (d, J=6.8 Hz, 6H) 1.45 (m, 1H), 1.76 (s, 3H), 1.81 (s, 3H), 1.88 (m, 1H), 2.04 (m, 1H), 2.24 (m, 1H), 2.54 (d. J=7.2 Hz, 2H), 3.77 (s, 3H), 3.98 (m, 2H), 4.55 (d, J=6.8 Hz, 2H), 4.64 (m, 1H), 4.82 (dd, J=4.4, 11.2 Hz, 1H), 5.49 (m, 1H), 6.98 (d, J=8.8 Hz, 2H), 7.53 (d, J=8.8 Hz, 2H); $^{13}$C NMR (CDCl$_3$, 100 MHz) δ 18.2, 21.2, 22.7, 23.2, 25.3, 25.8, 28.1, 32.8, 37.6, 52.8, 55.1, 62.8, 64.9, 114.8, 119.1, 121.0, 131.0, 137.9, 138.3, 138.7, 160.1, 169.7, 170.6, 171.2, 172.1. ESI-MS m/z 529 [M+H]$^+$.

Methyl 1-(2-(3-Isobutyl-4-(4-(3-methylbut-2-enyloxy)phenyl)-2,5-dioxo-2,5-dihydro-1H-pyrrol-1-yl)-4-methylpentanoyl)pyrrolidine-2-carboxylate (A1-4)

Obtained as yellow oil. $^1$H NMR (CDCl$_3$, 400 MHz) δ 0.89 (d, J=–6.4 Hz, 6H), 0.93 (d, J=6.4 Hz, 6H), 1.27 (t, J=7.2, 14 Hz, 3H), 1.41 (d, J=6.8 Hz, 3H), 1.44 (m, 1H), 1.76 (s, 3H), 1.79 (m, 1H), 1.81 (s, 3H), 2.04 (m, 1H), 2.30 (m, 1H), 2.53 (d, J=7.2 Hz, 2H), 4.16 (q, 2H), 4.53 (m, 1H), 4.55 (dd, J=7.2, 13.6 Hz, 3H), 4.77 (dd, J=5.2, 11.6 Hz, 1H), 5.49 (m, 1H), 6.98 (d, J=–8.8 Hz, 2H), 7.53 (d, J=8.8 Hz, 2H); $^{13}$C NMR (CDCl$_3$, 100 MHz) δ 14.1, 18.2, 18.4, 21.3, 22.7, 23.1, 25.4, 25.8, 28.0, 32.9, 37.6, 48.4, 53.3, 61.5, 64.9, 114.8, 119.2, 1212, 131.0, 137.7, 138.2, 138.7, 160.0, 169.1, 171.2, 172.0, 172.7. ESI-MS m/z 539 [M+H]$^+$.

Ethyl 2-(2-(3-isobutyl-4-(4-(3-methylbut-2-enyloxy)phenyl)-2,5-dioxo-2,5-dihydro-1H-pyrrol-1-yl)-4-methylpentanamido)propanoate (A1-5)

Obtained as yellow oil. $^1$H NMR (CDCl$_3$, 400 MHz) δ 0.89 (d, J=6.4 Hz, 6H), 0.96 (d, J=6.4 Hz, 6H), 1.28 (t, J=14 Hz, 3H), 1.46 (d, J=7.2 Hz, 3H) 1.56 (m, 1H), 1.71 (br s, 1H), 1.72 (s, 3H), 1.81 (s, 3H), 1.98 (m, 2H), 2.06 (m, 2H), 2.53 (d, J=–7.2 Hz, 2H), 2.58 (m, 1H), 3.57 (m, 2H), 4.50 (dd, J=–7.2, 13.6 Hz, 1H), 4.55 (d, 6.8 Hz, 2H), 4.91 (dd, J=5.2, 11.6 Hz, 1H), 5.49 (m, 1H), 6.96 (d, J=8.4 Hz, 2H), 7.51 (d, J=8.4 Hz, 2H); $^{13}$C NMR (CDCl$_3$, 100 MHz) δ 18.2, 21.3, 22.7, 22.7, 23.2, 25.1, 25.2, 25.8, 28.1, 28.8, 32.9, 36.4, 46.8, 51.6, 52.3, 64.8, 114.7, 119.2, 121.3, 131.0, 137.5, 138.0, 138.6, 159.9, 168.6, 171.1, 171.8, 172.4. ESI-MS m/z 527 [M+H]$^+$.

N-Cyclopropyl-2-(3-isobutyl-4-(4-(3-methylbut-2-enyloxy)phenyl)-2,5-dioxo-2,5-dihydro-1H-pyrrol-1-yl)-4-methylpentanamide (A1-6)

Obtained as yellow oil. $^1$H NMR (CDCl$_3$, 400 MHz) δ 0.49 (br s, 2H) 0.75 (d, J=6.8 Hz, 2H), 0.90 (d, J=6.4 Hz, 6H), 0.91 (d, J=6.4 Hz, 6H), 1.71 (m, 1H), 1.76 (s, 3H), 1.81 (s, 3H), 2.02 (m, 1H), 2.22 (m, 1H), 2.53 (d, J=7.2 Hz, 2H), 2.71 (m, 1H), 4.55 (d, J=6.8 Hz, 2H), 4.72 (dd, J=5.2, 7.6 Hz, 1H), 5.49 (m, 1H), 6.97 (d, J=8.4 Hz, 2H), 7.52 (d, J=8.4 Hz, 2H); $^{13}$C NMR (CDCl$_3$, 100 MHz) δ 6.6, 18.3, 21.3, 22.7, 23.1, 25.4, 25.8, 28.2, 32.9, 37.7, 53.7, 64.9, 114.8, 119.1, 121.3, 131.0, 137.7, 138.2, 138.7, 160.1, 171.0, 171.2, 172.1. ESI-MS m/z 467 [M+H]$^+$.

Methyl 2-(2-(3-isobutyl-4-(4-(3-methylbut-2-enyloxy)phenyl)-2,5-dioxo-2,5-dihydro-1H-pyrrol-1-yl)-3-phenylpropanamido)-4-methylpentanoate (A2-1)

Obtained as yellow oil. $^1$H NMR (CDCl$_3$, 400 MHz) (mixture of isomers) δ 0.75 (d, J=6.8 Hz, 3H), 0.77 (d, J=6.8 Hz, 3H), 0.94 (d, J=6 Hz, 6H), 1.54 (m, 1H), 1.64 (m, 1H), 1.75 (s, 3H), 1.77 (m, 1H), 1.81 (s, 3H), 1.87 (m, 1H), 2.39 (d, J=7.2 Hz, 2H), 3.47 (m, 2H), 3.71 (s, 3H), 4.53 (d, J=−6.4 Hz, 2H), 4.65 (m, 1H), 5.02 (dd, J=6.4, 10.4 Hz, 1H), 5.48 (t, J=7.6, 16.7 Hz, 1H), 6.94 (d, J=8.8 Hz, 2H), 7.23 (d, J=8 Hz, 2H), 7.34 (d, J=8 Hz, 2H), 7.36 (d, J=8.8 Hz, 2H). $^{13}$C NMR (CDCl$_3$, 100 MHz) δ 18.2, 21.9, 22.5, 22.7, 22.8, 24.8, 25.8, 28.0, 32.7, 34.9, 41.5, 50.9, 52.3, 55.9, 64.8, 114.7, 119.1, 120.9, 126.9, 128.5, 128.9, 130.8, 136.6, 137.8, 138.2, 138.7, 159.9, 168.6, 170.9, 171.7, 173.1; ESI-MS m/z 589 [M+H]$^+$.

Ethyl 2-(2-(3-isobutyl-4-(4-(3-methylbut-2-enyloxy)phenyl)-2,5-dioxo-2,5-dihydro-1H-pyrrol-1-yl)-3-phenylpropanamido)-3-phenylpropanoate. (A2-2)

Obtained as yellow oil. $^1$H NMR (CDCl$_3$, 400 MHz) (mixture of isomers) δ 0.76 (d, J=6.4 Hz, 3H), 0.74 (d, J=6.4 Hz, 3H), 1.22 (t, J=14 Hz, 3H), 1.76 (s, 3H), 1.81 (s, 3H), 1.87 (m, 1H), 2.38 (d, J=7.2 Hz, 2H), 3.18 (m, 2H), 3.40 (m, 2H), 4.14 (q, 2H), 4.54 (d, J 6.8 Hz, 2H), 4.85 (q, 1H), 4.95 (dd, J=6.8, 10.4 Hz, 1H), 5.49 (t, J=7.2, 16.7 Hz, 1H), 6.94 (d, J=8.8 Hz, 2H), 7.09 (d, J=8.4 Hz, 2H), 7.19 (m, 3H), 7.34 (d, J=8.8 Hz, 2H), 7.36 (d, J=8.8 Hz, 2H). $^{13}$C NMR (CDCl$_3$, 100 MHz) δ 14.1, 18.2, 22.5, 22.6, 25.8, 27.9, 32.7, 34.5, 37.9, 53.5, 55.8, 61.5, 64.8, 114.7, 119.1, 120.9, 126.8, 12.9, 128.4, 128.5, 128.9, 129.3, 130.8, 135.6, 136.6, 137.6, 138.1, 138.7, 159.9, 168.3, 170.8, 171.1, 171.5; ESI-MS m/z 637 [M+H]$^+$.

Ethyl 3-(4-hydroxyphenyl)-2-(2-(3-isobutyl-4-(4-(3-methylbut-2-enyloxy)phenyl)-2,5-dioxo-2,5-dihydro-1H-pyrrol-1-yl)-3-phenylpropanamido)propanoate (A2-3)

Obtained as yellow oil. $^1$H NMR (CDCl$_3$, 400 MHz) (mixture of isomers) δ 0.72 (d, J=6.8 Hz, 3H), 0.74 (d, J=6.8 Hz, 3H), 1.23 (t, J=14 Hz, 3H), 1.75 (s, 3H), 1.80 (s, 3H), 1.85 (m, 1H), 2.37 (d, J=7.2 Hz, 2H), 2.90 (dd, J=6.4, 11.0 Hz, 1H), 3.08 (dd, J=5.6, 14 Hz, 1H), 3.40 (m, 2H), 4.14 (q, 2H), 4.54 (d, J=6.4 Hz, 2H), 4.82 (q, 1H), 4.95 (dd. J=6.4, 10.8 Hz, 1H), 5.49 (t, J=7.2, 16.7 Hz, 1H), 6.65 (d, J=8.8 Hz, 2H), 6.93 (d, J=8 Hz, 2H), 6.95 (d, J-8 Hz, 2H), 7.15 (m, 3H), 7.36 (d, J=8.4 Hz, 2H), 7.36 (d, J=Hz, 2H). $^{13}$C NMR (CDCl$_3$, 100 MHz) δ 14.1, 18.2, 22.5, 22.6, 25.8, 27.9, 32.7, 34.5, 37.1, 53.6, 55.8, 61.6, 64.9, 114.7, 115.4, 119.1, 120.9, 126.9, 127.4, 128.5, 128.9, 130.5, 130.9, 136.5, 137.6, 138.1, 138.7, 154.8, 159.9, 168.5, 170.8, 171.2, 171.5; ESI-MS m/z 653 [M+H]$^+$.

Methyl 1-(2-(3-isobutyl-4-(4-(3-methylbut-2-enyloxy)phenyl)-2,5-dioxo-2,5-dihydro-1H-pyrrol-1-yl)-3-phenylpropanoyl)pyrrolidine-2-carboxylate (A2-4)

Obtained as yellow oil. $^1$H NMR (CDCl$_3$, 400 MHz) δ 0.78 (d, J=6.4 Hz, 3H), 0.82 (d, J=6.4 Hz, 6H), 1.75 (s, 3H), 1.80 (s, 3H), 1.91 (m, 2H), 2.06 (m, 2H), 2.41 (d, J=7.2 Hz, 2H), 3.37 (m, 2H), 3.58 (m, 2H), 3.71 (s, 3H), 4.50 (dd, J=Hz, 1H), 4.54 (d, J=6.4 Hz, 2H), 5.07 (dd, J=Hz, 1H), 5.48 (m, 1H), 6.92 (d, J=8.4 Hz, 2H), 7.12-7.24 (m, 5H), 7.39 (d, J=8.4 Hz, 2H); $^{13}$C NMR (CDCl$_3$, 100 MHz) δ 18.2, 22.5, 22.7, 24.9, 25.8, 27.9, 28.7, 32.7, 34.3, 46.9, 52.3, 53.9, 59.4, 64.8, 114.7, 119.2, 121.1, 126.7, 128.7, 129.3, 130.9, 137.2, 137.3, 137.8, 138.7, 159.9, 167.4, 170.5, 171.2, 172.6. ESI-MS m/z 573 [M+H].

N-Cyclopropyl-2-(3-isobutyl-4-(4-(3-methyl but-2-enyloxy)phenyl)-2,5-dioxo-2,5-dihydro-1H-pyrrol-1-yl)-3-phenylpropanamide (A2-5)

Obtained as yellow oil. $^1$H NMR (CDCl$_3$, 400 MHz) δ 0.49 (br s, 2H), 0.72 (d, J=6.8 Hz, 2H), 0.76 (d, J=6.8 Hz, 12H), 1.75 (s, 3H), 1.81 (s, 3H), 1.85 (m, 2H), 2.66 (d, J=7.6 Hz, 2H), 2.72 (m, 1H), 3.45 (m, 2H), 4.53 (d, J=7.2 Hz, 2H), 4.94 (dd, J=5.2, 10.8 Hz, 1H), 5.49 (m, 1H), 6.94 (d, J=8.4 Hz, 2H), 7.14 (m, 3H), 7.20 (d, J=8 Hz, 2H), 7.35 (d, J=8.4 Hz, 2H); $^{13}$C NMR (CDCl$_3$, 100 MHz) δ 6.5, 6.6, 18.2, 22.5, 22.6, 22.8, 25.8, 27.9, 32.7, 34.9, 56.3, 64.8, 114.8, 119.1, 120.9, 126.9, 128.6, 128.9, 130.8, 136.6, 137.7, 138.1, 138.7, 159.9, 170.2, 171.1, 171.7. ESI-MS m/z 501[M+H]$^+$.

(3) General Method for the Preparation of Compounds KA-1~KA-4, KB-1 and KC-1~KC-3

First step, the same method as in the preparation of compound A1-1 was used to obtain compounds KA-1~KA-4, KB-1 and KC-1~KC-3. Without purification, to the product from the previous step (1.6 mmol) in anhydrous dichloromethane (70 mL) was added Dess-Martin periodinane (2.4 mmol) and the mixture was stirred for 18 hrs. The reaction was stopped by adding 10% sodium thiosulfate (35 mL) and saturated sodium bicarbonate solution (35 mL) and stirred for 30 min. the chloroform layer was separated and washed with brine (1×10 mL) and evaporated in vacuum. The resulting compound was purified on silica gel column using Hexane: ethyl acetate 9.5:0.5 v/v.

Methyl 2-(3-(3-isobutyl-4-(4-(3-methylbut-2-enyloxy)phenyl)-2,5-dioxo-2,5-dihydro-1H-pyrrol-1-yl)-2-oxopropanamido)-3-methylbutanoate (KA-1)

Obtained as yellow oil. $^1$H NMR (CDCl$_3$, 400 MHz) 0.90 (d, J=6.4 Hz, 6H), 0.96 (d, J=6.4 Hz, 6H), 1.76 (s, 3H), 1.81 (s, 3H), 2.07 (m, 1H), 2.24 (m, 1H), 2.55 (d, J=7.2 Hz, 2H), 3.8 (s, 3H), 4.50 (dd, J=4.8, 8.8 Hz, 1H), 4.55 (d, J=6.8 Hz, 1H), 4.96 (s, 2H), 5.49 (t, J=7.2, 16 Hz, 1H), 6.98 (d, J=9.2 Hz, 2H), 7.53 (d, J=8.8 Hz, 2H); $^{13}$C NMR (CDCl$_3$, 100 MHz) δ 17.7, 18.2, 18.9, 22.7, 25.8, 28.1, 31.4, 32.9, 43.9, 52.4, 57.2, 64.9, 114.8, 119.2, 121.2, 130.9, 138.2, 138.6, 138.7, 158.5, 160.0, 170.5, 170.9, 171.3, 190.3. ESI-MS m/z 513 [M+H]$^+$.

Ethyl 2-(3-(3-isobutyl-4-(4-(3-methylbut-2-enyloxy)phenyl)-2,5-dioxo-2,5-dihydro-1H-pyrrol-1-yl)-2-oxopropanamido)-3-phenylpropanoate (KA-2)

Obtained as yellow oil. $^1$H NMR (CDCl$_3$, 400 MHz) δ 0.90 (d, J=6.4 Hz, 6H), 1.23 (t, J=6.8, 14 Hz, 3H), 1.76 (s, 3H), 1.81 (s, 3H), 2.06 (m, 1H), 2.54 (d, J=7.2 Hz, 2H), 3.15 (d, J=6 Hz, 2H), 4.18 (m, 2H), 4.55 (d, J=6.4 Hz, 1H), 4.82 (m, 1H), 4.92 (s, 2H), 5.49 (m, 1H), 6.98 (d, J=8.8 Hz, 2H), 7.12 (d, J=8 Hz, 2H), 7.26 (m, 3H), 7.53 (d, J=8.8 Hz, 2H); $^{13}$C NMR (CDCl$_3$, 100 MHz) δ 14.1, 18.3, 22.7, 25.8, 28.1, 32.9, 38.0, 43.8, 53.2, 61.9, 64.9, 114.8, 119.2, 121.2, 127.4, 128.7, 129.2, 130.9, 135.0, 138.3, 138.6, 138.7, 158.2, 160.0, 170.1, 170.5, 171.2, 190.1. ESI-MS m/z 575 [M+H]$^+$.

Ethyl 2-(3-(3-isobutyl-4-(4-(3-methylbut-2-enyloxy)phenyl)-2,5-dioxo-2,5-dihydro-1H-pyrrol-1-yl)-2-oxopropanamido)propanoate (KA-3)

Obtained as yellow oil. $^1$H NMR (CDCl$_3$, 400 MHz) δ 0.91 (d, J=6.8 Hz, 6H), 1.28 (t, J=7.2, 14 Hz, 3H), 1.46 (d, J=7.2

Hz, 3H), 1.76 (s, 3H), 1.81 (s, 3H), 2.07 (m, 1H), 2.54 (d, J=7.6 Hz, 2H), 4.23 (q, 2H), 4.56 (d, J=6.4 Hz, 2H), 4.92 (s, 2H), 5.49 (t, J=7.2, 16.7 Hz, 1H), 6.99 (d, J=8.4 Hz, 2H), 7.53 (d, J=8.4 Hz, 2H); $^{13}$C NMR (CDCl$_3$, 100 MHz) δ 14.1, 18.1, 18.3, 22.7, 25.8, 28.1, 32.9, 43.8, 48.1, 61.9, 64.9, 114.8, 119.2, 121.2, 130.9, 138.2, 138.6, 138.7, 158.1, 160.0, 170.5, 171.3, 171.5, 190.3. ESI-MS m/z 499 [M+H]$^+$.

N-Cyclopropyl-3-(3-isobutyl-4-(4-(3-methylbut-2-enyloxy)phenyl)-2,5-dioxo-2,5-dihydro-1H-pyrrol-1-yl)-2-oxopropanamide (KA-4)

Obtained as yellow oil. $^1$H NMR (CDCl$_3$, 400 MHz) δ 0.62 (br s, 2H), 0.85 (d, J=5.6 Hz, 2H), 0.91 (d, J=6.4 Hz, 6H), 1.76 (s, 3H), 1.81 (s, 3H), 2.07 (m, 1H), 2.55 (d, J=7.2 Hz, 2H), 2.78 (m, 1H), 4.55 (d, J=6.8 Hz, 2H), 4.96 (s, 2H), 5.49 (t, J=7.2, 16 Hz, 1H), 6.98 (d, J=8.8 Hz, 2H), 7.52 (d, J=8.8 Hz, 2H); $^{13}$C NMR (CDCl$_3$, 100 MHz) δ 6.5, 18.2, 22.4, 22.7, 25.8, 28.1, 32.9, 43.8, 64.9, 114.8, 119.2, 121.2, 130.9, 138.2, 138.5, 138.7, 160.0, 160.1, 171.3, 190.9. ESI-MS m/z 439 [M+H]$^+$.

N-Cyclopropyl-4-(3-isobutyl-4-(4-(3-methylbut-2-enyloxy)phenyl)-2,5-dioxo-2,5-dihydro-1H-pyrrol-1-yl)-2-oxobutanamide (KB-1)

Obtained as yellow oil. $^1$H NMR (CDCl$_3$, 400 MHz) δ 0.59 (br s, 2H), 0.83 (d, J=5.6 Hz, 2H), 0.89 (d, J=6.4 Hz, 6H), 1.76 (s, 3H), 1.81 (s, 3H), 2.03 (m, 1H), 2.49 (d, J=7.6 Hz, 2H), 2.76 (m, 1H), 3.2 (t, J=6.8, 13.6 Hz, 2H), 3.9 (t, J=6.8, 13.6 Hz, 2H), 4.55 (d, J=6.8 Hz, 2H), 5.49 (t, J=7.2, 16 Hz, 1H), 6.97 (d, J=8.8 Hz, 2H), 7.49 (d, J=8.8 Hz, 2H); $^{13}$C NMR (CDCl$_3$, 100 MHz) δ 6.5, 18.2, 22.4, 22.7, 25.8, 28.1, 32.8, 32.9, 35.8, 64.8, 114.7, 119.2, 121.3, 130.9, 137.9, 138.2, 138.7, 159.9, 160.9, 171.0, 171.7, 196.6. ESI-MS m/z 453 [M+H]$^+$.

Ethyl 2-(3-(3-isobutyl-4-(4-(3-methylbut-2-enyloxy)phenyl)-2,5-dioxo-2,5-dihydro-1H-pyrrol-1-yl)-2-oxo-3-phenylpropanamido)-3-phenylpropanoate (KC-1)

Obtained as yellow oil. $^1$H NMR (CDCl$_3$, 400 MHz) δ 0.88 (d, J=6.4 Hz, 3H), 0.91 (d, J=6.4 Hz, 3H), 1.20 (t, J=7.2, 14 Hz, 3H), 1.76 (s, 3H), 1.80 (s, 3H), 2.04 (m, 1H), 2.51 (d, J=7.2 Hz, 2H), 3.11 (m, 2H), 4.14 (q, J=Hz, 2H), 4.53 (d, J=6.8 Hz, 2H), 4.72 (m, 1H), 5.49 (t, J=7.2, 16 Hz, 1H), 6.30 (s, 1H), 6.35 (s, 1H), 6.95 (d, J=8.8 Hz, 2H), 7.28 (br s, 5H), 7.36 (br s, 5H), 7.51 (d, J=8.8 Hz, 2H); ESI-MS m/z 651 [M+H]$^+$.

Ethyl 2-(3-(3-isobutyl-(4-(3-methylbut-2-enyloxy)phenyl)-2,5-dioxo-2,5-dihydro-1H-pyrrol-1-yl)-2-oxo-3-phenylpropanamido)propanoate (KC-2)

Obtained as yellow oil. $^1$H NMR (CDCl$_3$, 400 MHz) δ 0.88 (d, J=6.4 Hz, 6H), 1.25 (t, J=7.2, 14 Hz, 3H), 1.41 (d, J=6.8 Hz, 3H), 1.76 (s, 3H), 1.80 (s, 3H), 2.04 (m, 1H), 2.51 (d, J=7.2 Hz, 2H), 4.19 (m, 2H), 4.44 (m, 1H), 4.53 (d, J=6.8 Hz, 2H), 5.49 (t, J=7.2, 16 Hz, 1H), 6.3 (s, 1H), 6.32 (s, 1H), 6.95 (d, J=8.8 Hz, 2H), 7.36 (br s, 5H), 7.51 (d, J=8.4 Hz, 2H); $^{13}$C NMR (CDCl$_3$, 100 MHz) δ 14.1, 17.9, 17.9, 18.2, 22.7, 25.8, 28.1, 32.9, 48.2, 48.3, 58.6, 61.7, 61.8, 64.9, 114.8, 119.2, 121.1, 121.2, 128.7, 128.9, 129.2, 129.3, 130.9, 131.0, 133.7, 138.1, 138.4, 138.5, 138.7, 158.9, 159.1, 159.9, 171.3, 171.5, 191.4. ESI-MS m/z 575 [M+H]$^+$.

(4) Compounds A1~A9, A1-1~A1-5 and A2-1~A2-4 were Prepared According to the Process Outlined in Scheme 1 as Shown Below.

Scheme 1

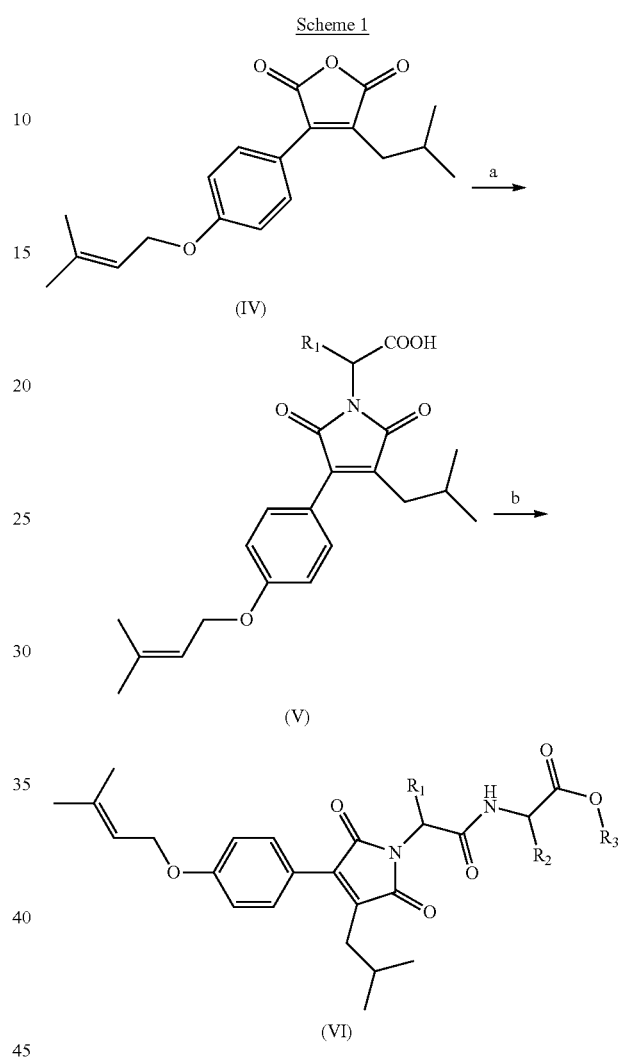

Reaction conditions: (a) amino acid, DMF, 1400° C.; (b) Amino acid ester, DMF, HOBT, triethylamine, 0° C., EDC, rt 18 hrs.

Representative compounds of Scheme 1 were as listed in Tables 1-2, below.

TABLE 1

Representative Compounds of Formula (V)

| $R_1$ | Compound No. |
| --- | --- |
| —CH$_2$—CH—(CH$_3$)$_2$ | A1 |
| —CH$_2$—Ph | A2 |
| —CH$_2$—OH | A3 |
| —CH$_2$-(p-OH—Ph) | A4 |
| —(CH$_2$)$_2$—SH—CH$_3$ | A5 |
| —CH(OH)—CH$_3$ | A6 |
| —CH—(CH$_3$)$_2$ | A7 |
| —CH$_3$ | A8 |
| —(CH$_2$)$_2$—COOH | A9 |

TABLE 2

Representative Compounds of Formula (VI)

| R₁ | R₂ | R₃ | Compound No. |
|---|---|---|---|
| —CH₂—CH—(CH₃)₂ | —CH—(CH₃)₂ | Me | A1-1 |
| —CH₂—CH—(CH₃)₂ | —CH₂-(p-OH—Ph) | Ethyl | A1-2 |
| —CH₂—CH—(CH₃)₂ | —CH₂—OH | Me | A1-3 |
| —CH₂—CH—(CH₃)₂ | Proline | Me | A1-4 |
| —CH₂—CH—(CH₃)₂ | —CH₃ | Ethyl | A1-5 |
| —CH₂—Ph | —CH₂—CH—(CH₃)₂ | Me | A2-1 |
| —CH₂—Ph | —CH₂—Ph | Ethyl | A2-2 |
| —CH₂—Ph | —CH₂—P—OHPh | Ethyl | A2-3 |
| —CH₂—Ph | Proline | Me | A2-4 |

(5) Compounds KA~KC, KA-1~KA-3 and KC-1~KC-2 were Prepared According to the Process Outlined in Scheme 2 as Shown Below.

Scheme 2

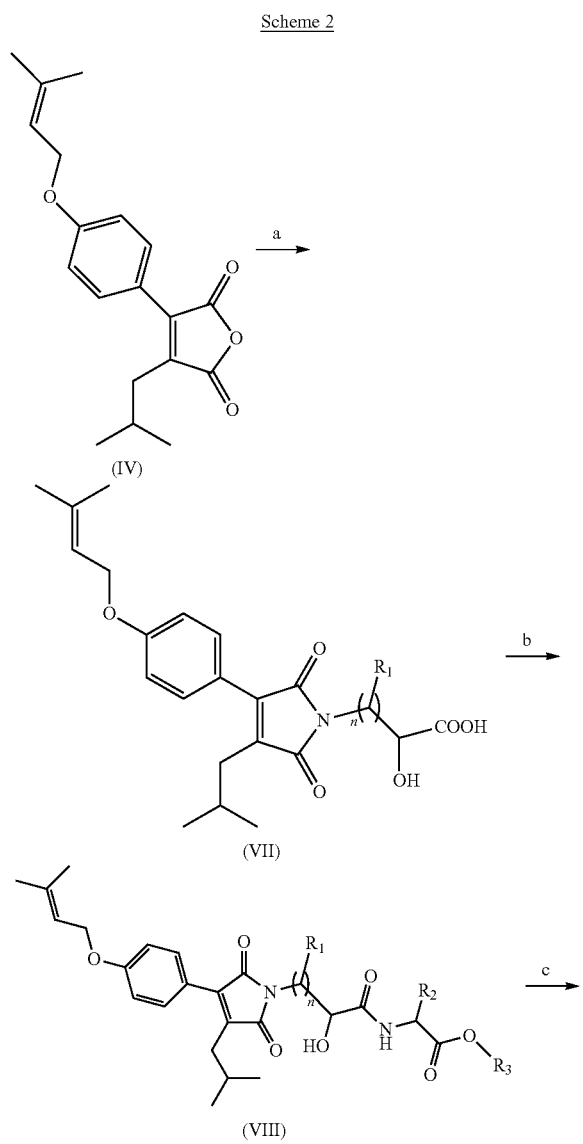
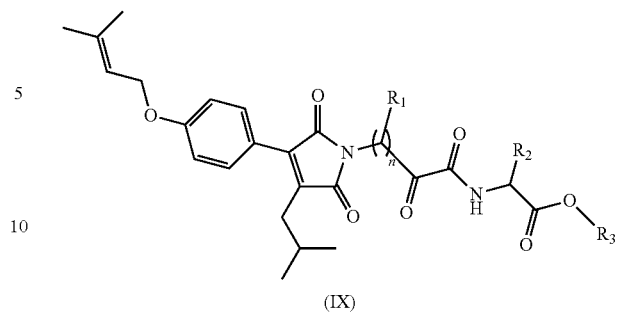

Reaction conditions: (a) amino acid, DMF, 140° C.; (b) Amino acid ester, DMF, HOBT, tri-ethylamine, 0° C., EDC, rt 18 hrs; (c) Dess-martin periodinane, CH₂Cl₂, rt, 18 hrs.

Representative compounds of Scheme 2 were as listed in Tables 3-5, below.

TABLE 3

Representative Compounds of Formula (VII)

| n | R₁ | Compound No. |
|---|---|---|
| 1 | —H | KA |
| 2 | —H | KB |
| 1 | Phenyl | KC |

TABLE 4

Representative Compounds of Formula (VIII)

| n | R₁ | R₂ | R₃ | Compound No. |
|---|---|---|---|---|
| 1 | —H | —CH—(CH₃)₂ | Me | None |
| 1 | —H | —CH₂—Ph | Ethyl | None |
| 1 | —H | —CH₃ | Ethyl | None |
| 1 | Phenyl | —CH₂—Ph | Ethyl | None |
| 1 | Phenyl | —CH₃ | Ethyl | None |

TABLE 5

Representative Compounds of Formula (IX)

| n | R₁ | R₂ | R₃ | Compound No. |
|---|---|---|---|---|
| 1 | —H | —CH—(CH₃)₂ | Me | KA-1 |
| 1 | —H | —CH₂—Ph | Ethyl | KA-2 |
| 1 | —H | —CH₃ | Ethyl | KA-3 |
| 1 | Phenyl | —CH₂—Ph | Ethyl | KC-1 |
| 1 | Phenyl | —CH₃ | Ethyl | KC-2 |

(6) Compounds KB-1, KC-3, A1-6 and A2-5 were Prepared According to the Process Outlined in Scheme 3 as Shown Below.

Scheme 3

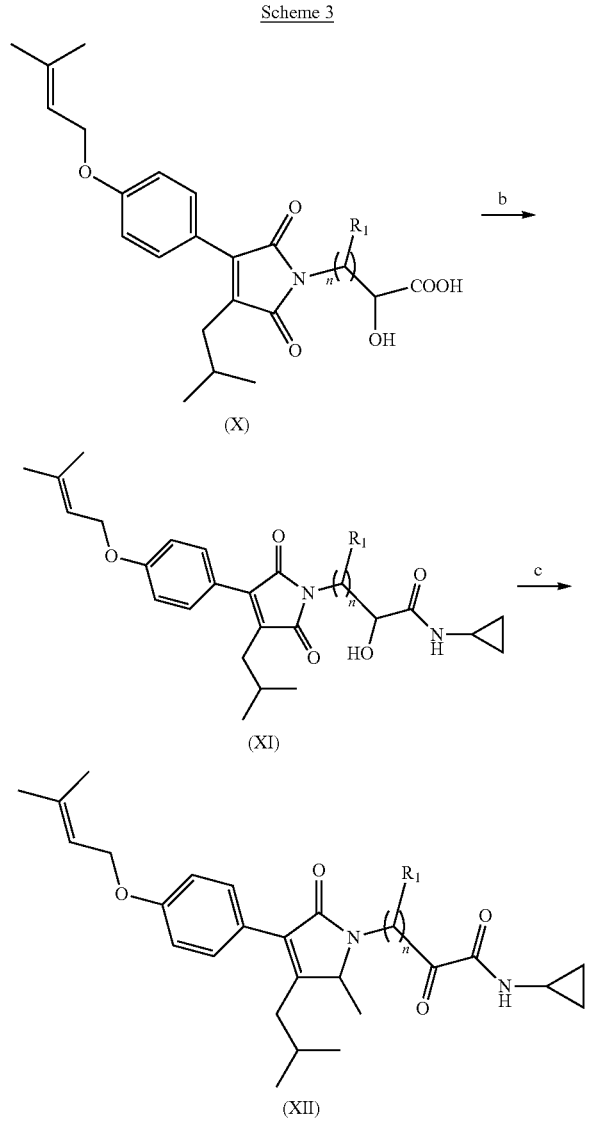

(X)

(XI)

(XII)

Reaction conditions: (b) Amino acid ester, DMF, HOBT, tri-ethylamine, 0° C., EDC, rt 18 has; (c) Dess-martin periodinane, CH$_2$Cl$_2$, rt, 18 hrs.

Representative compounds of Scheme 3 were as listed in Tables 6-8, below.

TABLE 6

Representative Compounds of Formula (X)

| n | R$_1$ | Compound No. |
|---|---|---|
| 1 | Phenyl | None |
| 2 | —H | None |
| 1 | —CH$_2$—CH—(CH$_3$)$_2$ | None |
| 1 | —CH$_2$—Ph | None |

TABLE 7

Representative Compounds of Formula (XI)

| n | R$_1$ | Compound No. |
|---|---|---|
| 1 | Phenyl | None |
| 2 | —H | None |
| 1 | —CH$_2$—CH—(CH$_3$)$_2$ | None |
| 1 | —CH$_2$—Ph | None |

TABLE 8

Representative Compounds of Formula (XII)

| n | R$_1$ | Compound No. |
|---|---|---|
| 1 | Phenyl | KC-3 |
| 2 | H | KB-1 |
| 1 | —CH$_2$—CH—(CH$_3$)$_2$ | A1-6 |
| 1 | —CH$_2$—Ph | A2-5 |

(7) The R$_3$ group of the compounds of formula (I) was prepared from the method as described in reference (Stewart et al., 2007, A concise synthesis of maleic anhydride and maleimide natural products found in *Antrodia camphorate*. Tetrahedron Letters, 48, 2241-2244; Cheng et al., 2008, Total synthesis of (±)-camphorataimides and (±)-himanimides by NaBH$_4$/Ni(OAc)$_2$ or Zn/AcOH stereoselective reduction. Tetrahedron, 64, 4347-4353).

Example 2

HCV Protease Assay

The HCV protease assay herein was applied to investigate the HCV-protease inhibitory activity of the prepared compounds as described above. The method of the HCV protease assay was described in D. T. Phuong, C. M. Ma, M. Hattori and J. S. Jin: Inhibitory Effects of Antrodins A-E from *Antrodia cinnamomea* and Their Metabolites on Hepatitis C Virus Protease. Phytotherapy Research, 23, 582-584, 2009. Two micro liters of a compound solution (using DMSO as solvent) was placed in 384 well micro plate, then 8 µl of HCV NS3/4A protease (0.5 g/mL) was added to the well containing a sample and the plate was agitated. Finally, 10 µL of freshly prepared substrate (Ac-Asp-Glu-Dap(QXL™ 520)-Glu-Glu-Abu-COO-Ala-Ser-Cys(5-FAMsp)-NH$_2$) (100× dilution of a DMSO stock solution) was added with sequential rotational shaking. The reaction mixture was incubated for 30 min at 37° C. The fluorimetric analyses were performed on an automated TECAN GENios plate reader with excitation wavelength at 485 nm and emission at 530 nm. Each test compound was carried out in triplicate. The HCV-PR inhibition (%) was calculated by using the following equation:

% inhibition=($F_{vehicle}$ control−$F_{substrate}$ control)×100/$F_{vehicle}$ control (Where F is the fluorescence value of vehicle control or of sample minus the fluorescence of the substrate control).

The results were shown in Table 9.

In addition, the dipeptidyl peptidase-IV (DPPIV) assay herein was applied to investigate the DPPIV inhibitory activity of the prepared compounds as described above. The method of the DPPIV assay was described in Lin et al., 1998. Inhibition of dipeptidyl peptidase IV by fluoroolefin-containing N-peptidyl-O-hydroxylamine peptidomimetics. Proc.

Natl. Acad. Sci. USA Vol. 95, pp. 14020-14024. The DPPIV inhibition (%) was calculated by using the following equation:

% inhibition=$[(1-v_i/v_0)] \times 100$ (Where $v_i$ and $v_0$ are the $V_{max}$ value of test compound and control, respectively).

The results were shown in Table 10.

TABLE 9

IC$_{50}$ values of the compounds against HCV protease.

| Compound No. | R | IC$_{50}$ (µM) |
| --- | --- | --- |
| A1 | *isobutyl-CH(COOH)-* | 8.6 |
| A2 | *benzyl-CH(COOH)-* | 14.0 |
| A3 | *HOCH$_2$-CH(COOH)-* | 27.0 |
| A4 | *4-hydroxybenzyl-CH(COOH)-* | 16.0 |
| A5 | *CH(OH)(CH$_3$)-CH(COOH)-* | 21.0 |
| A6 | *isopropyl-CH(COOH)-* | 18.0 |

TABLE 9-continued

| ID | Structure | Value |
|----|-----------|-------|
| A7 | (2-methylpropanoic acid fragment) | 23.3 |
| A8 | (2-(2-carboxyethyl)propanedioic acid fragment) | 27.0 |
| A9 | (2-(2-(methylthio)ethyl)carboxylic acid fragment) | 19.0 |
| KA | (2-hydroxy-propanoic acid ethyl fragment) | 8.7 |
| KB | (2-hydroxy-butanoic acid propyl fragment) | 15.6 |
| KC | (2-hydroxy-3-phenylpropanoic acid fragment) | 5.0 |
| A1-1 | (leucine-valine methyl ester fragment) | >100 |

TABLE 9-continued
| | | |
|---|---|---|
| A1-2 | 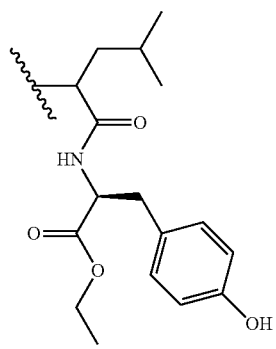 [SMILES: *C(CC(C)C)C(=O)N[C@@H](Cc1ccc(O)cc1)C(=O)OCC] | >100 |
| A1-3 | 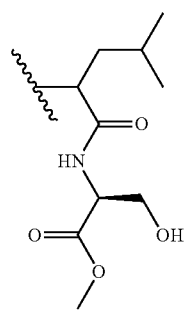 [SMILES: *C(CC(C)C)C(=O)N[C@@H](CO)C(=O)OC] | >100 |
| A1-4 | 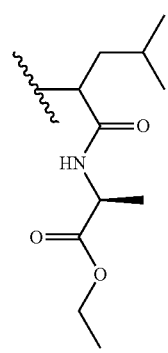 [SMILES: *C(CC(C)C)C(=O)N[C@@H](C)C(=O)OCC] | >100 |
| A2-1 | 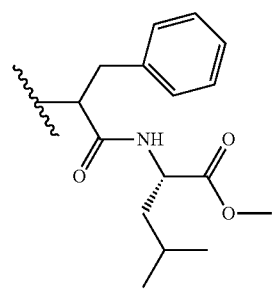 [SMILES: *C(Cc1ccccc1)C(=O)N[C@@H](CC(C)C)C(=O)OC] | >100 |
| A2-2 | 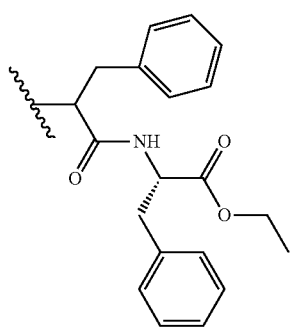 [SMILES: *C(Cc1ccccc1)C(=O)N[C@@H](Cc1ccccc1)C(=O)OCC] | 100 |

TABLE 9-continued
| | | |
|---|---|---|
| A2-3 | 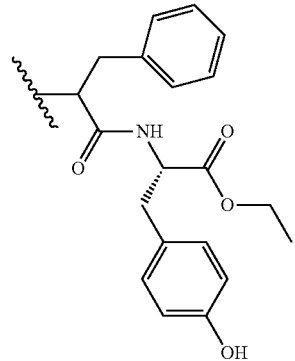 [SMILES: *C(Cc1ccccc1)C(=O)N[C@@H](Cc1ccc(O)cc1)C(=O)OCC] | 100 |
| A1-6-ter | 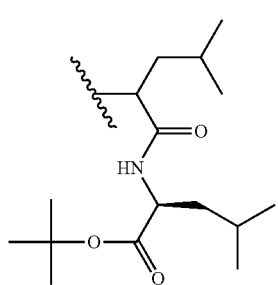 [SMILES: *C(CC(C)C)C(=O)N[C@@H](CC(C)C)C(=O)OC(C)(C)C] | >200 |
| A1-7-ter | 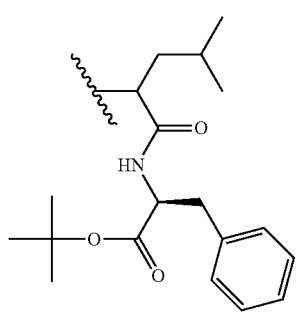 [SMILES: *C(CC(C)C)C(=O)N[C@@H](Cc1ccccc1)C(=O)OC(C)(C)C] | >200 |
| A1-10-ter | 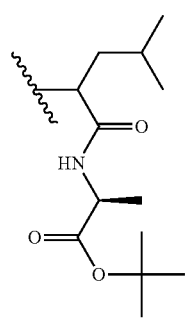 [SMILES: *C(CC(C)C)C(=O)N[C@@H](C)C(=O)OC(C)(C)C] | >200 |
| A2-11-ter | 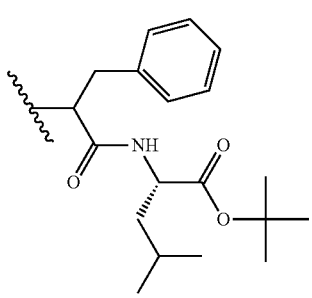 [SMILES: *C(Cc1ccccc1)C(=O)N[C@@H](CC(C)C)C(=O)OC(C)(C)C] | >200 |

TABLE 9-continued

| KB-3 | [structure: wavy-CH2-C(=O)-C(=O)-NH-cyclopropyl] | >100 |
| KC-1 | [structure: wavy-CH(Bn)-C(=O)-C(=O)-NH-CH(Bn)-C(=O)-O-ethyl] | >100 |
| KC-2 | [structure: wavy-CH(Bn)-C(=O)-C(=O)-NH-CH(CH3)-C(=O)-O-ethyl] | >100 |
| KC-3 | [structure: wavy-CH(Ph)-C(=O)-C(=O)-NH-cyclopropyl] | >100 |
| KAnh-1 | [structure: wavy-CH2-C(=O)-C(=O)-NH2] | 153 |
| KBnh-1 | [structure: wavy-CH2CH2-C(=O)-C(=O)-NH2] | 12.1 |
| KCnh-1 | [structure: wavy-CH(Ph)-C(=O)-C(=O)-NH2] | 1.95 |
| KA-5-2 | [structure: wavy-CH2-C(=O)-C(=O)-NH-CH(CH3)-C(=O)-O-tBu] | 47.6 |
| KB-1-2 | [structure: wavy-CH2CH2-C(=O)-C(=O)-NH-CH(CH3)-C(=O)-O-tBu] | 35.2 |

TABLE 9-continued
| | | |
|---|---|---|
| KB-2-2 | 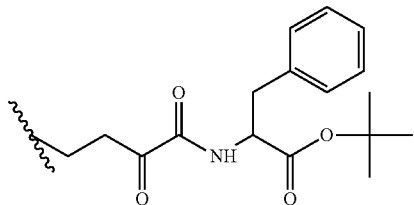 [SMILES: *CCC(=O)C(=O)NC(Cc1ccccc1)C(=O)OC(C)(C)C] | 16.2 |
| KC-4-2 | 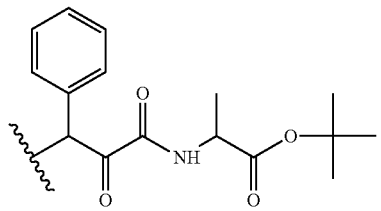 [SMILES: *C(C(=O)C(=O)NC(C)C(=O)OC(C)(C)C)c1ccccc1] | 18.3 |
| KC-5-2 | 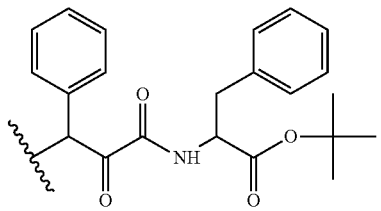 [SMILES: *C(C(=O)C(=O)NC(Cc1ccccc1)C(=O)OC(C)(C)C)c1ccccc1] | 51.6 |
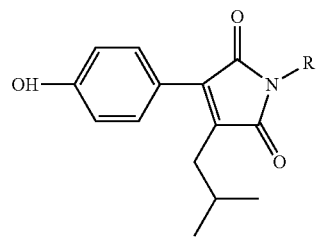
| Compound No. | R | IC$_{50}$ (μM) |
|---|---|---|
| A10 | 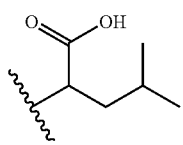 [SMILES: *C(CC(C)C)C(=O)O] | >200 |
| A11 | 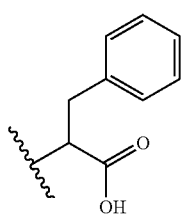 [SMILES: *C(Cc1ccccc1)C(=O)O] | 63 |
| A12 | 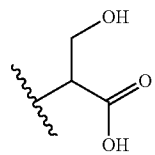 [SMILES: *C(CO)C(=O)O] | 25 |

TABLE 9-continued
| | | |
|---|---|---|
| A13 | 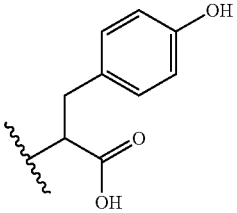 [SMILES: *C(Cc1ccc(O)cc1)C(=O)O] | >200 |
| A14 | 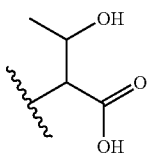 [SMILES: *C(C(=O)O)C(C)O] | >200 |
| A15 | 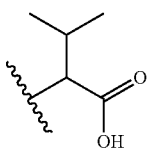 [SMILES: *C(C(=O)O)C(C)C] | 85 |
| A16 | 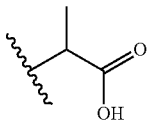 [SMILES: *C(C)C(=O)O] | 170 |
| A17 | 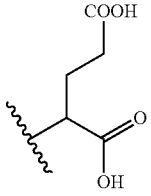 [SMILES: *C(CCC(=O)O)C(=O)O] | 105 |
| KA-t | 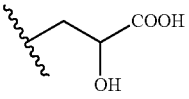 [SMILES: *CC(O)C(=O)O] | 185 |
| KB-t | 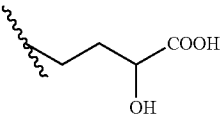 [SMILES: *CCC(O)C(=O)O] | 75 |
| KC-t | 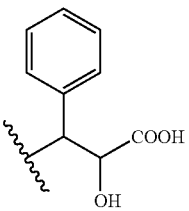 [SMILES: *C(c1ccccc1)C(O)C(=O)O] | 73 |
| A1-6 | 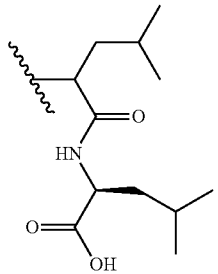 [SMILES: *C(CC(C)C)C(=O)N[C@@H](CC(C)C)C(=O)O] | >200 |

TABLE 9-continued
| | | |
|---|---|---|
| A1-7 | 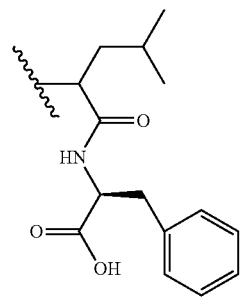 [SMILES: *C(CC(C)C)C(=O)N[C@@H](Cc1ccccc1)C(=O)O] | 27 |
| A1-10 | 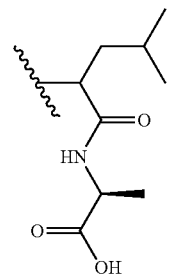 [SMILES: *C(CC(C)C)C(=O)N[C@@H](C)C(=O)O] | 16 |
| A2-11 | 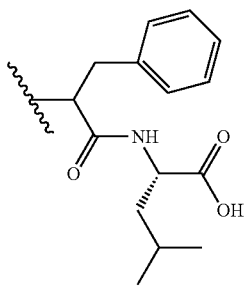 [SMILES: *C(Cc1ccccc1)C(=O)N[C@@H](CC(C)C)C(=O)O] | 120 |
| A2-12 | 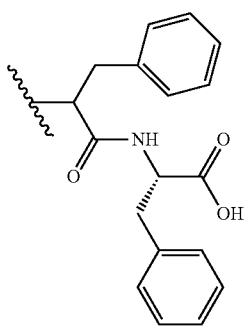 [SMILES: *C(Cc1ccccc1)C(=O)N[C@@H](Cc1ccccc1)C(=O)O] | 192 |
| A3-16 | 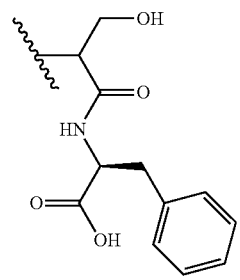 [SMILES: *C(CO)C(=O)N[C@@H](Cc1ccccc1)C(=O)O] | 132 |
| KAnh-2 | 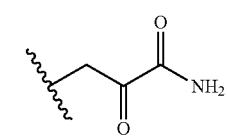 [SMILES: *CC(=O)C(N)=O] | 145.5 |

TABLE 9-continued
| | | |
|---|---|---|
| KBnh-2 | 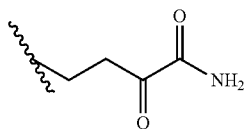 [SMILES: *CCC(=O)C(N)=O] | 7.4 |
| KCnh-2 | 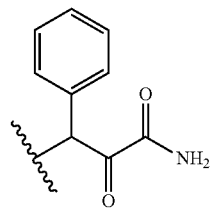 [SMILES: *C(C(=O)C(N)=O)c1ccccc1] | 1.4 |
| KA-5 | 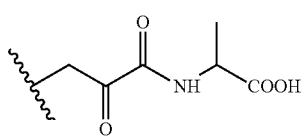 [SMILES: *CC(=O)C(=O)NC(C)C(=O)O] | 70 |
| KB-1 | 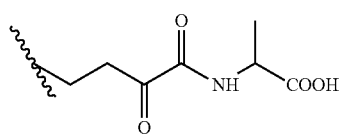 [SMILES: *CCC(=O)C(=O)NC(C)C(=O)O] | 61.9 |
| KB-2 | 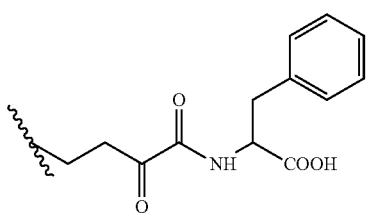 [SMILES: *CCC(=O)C(=O)NC(Cc1ccccc1)C(=O)O] | 100 |
| KC-4 | 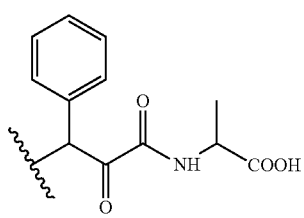 [SMILES: *C(C(=O)C(=O)NC(C)C(=O)O)c1ccccc1] | 14.6 |
| KC-5 | 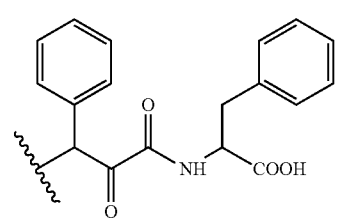 [SMILES: *C(C(=O)C(=O)NC(Cc1ccccc1)C(=O)O)c1ccccc1] | 9 |

TABLE 10
IC50 values of the compounds against DPPIV
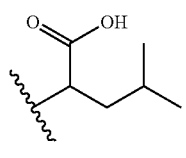
| Compound No. | R | IC50 (μg/ml) |
|---|---|---|
| Antrodin A | X=O | 25 |
| Antrodin B | X=N | 50 |
| Antrodin C | X=N, R=OH | 38 |
| A1 | 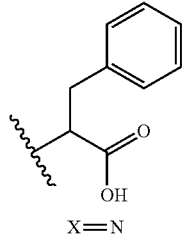 X=N | 45 |
| A2 | 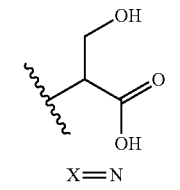 X=N | 35 |
| A3 | 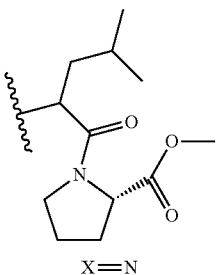 X=N | 40 |
| A1-5 | 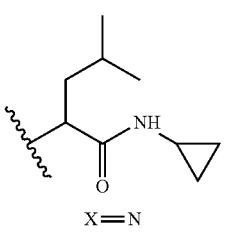 X=N | >100* 35* |
| A1-8 | 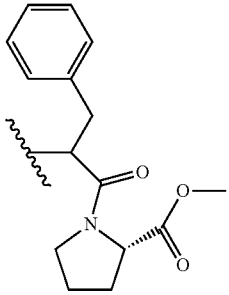 X=N | >100* 50* |
TABLE 10-continued
| | | |
|---|---|---|
| A2-6 | 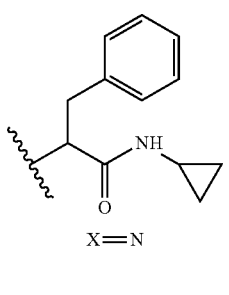 X=N | 89.0* 70* |
| A2-8 | 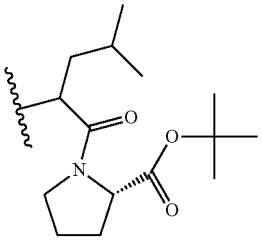 X=N | >100* 43* |
| A1-9-ter | 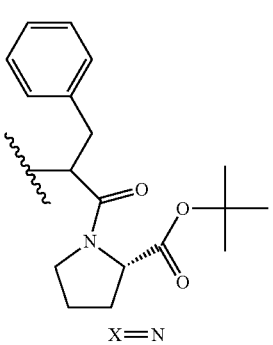 X=N | 60 |
| A2-14-ter | 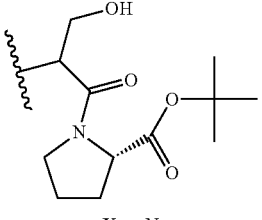 X=N | 84 |
| A3-15-ter | X=N | 55 |

TABLE 10-continued

[Structure: 4-hydroxyphenyl substituted pyrrole/furan dione with isobutyl group and R substituent]

| Comp No. | R | IC$_{50}$ (μM) |
|---|---|---|
| A1-t | [leucine-like with COOH, X=N] | 75 |
| A2-t | [phenylalanine-like with COOH, X=N] | 90 |
| A3-t | [serine-like with OH and COOH, X=N] | 70 |
| A1-9 | [leucine-proline dipeptide, X=N] | 29 |
| A2-14 | [phenylalanine-proline dipeptide, X=N] | 60 |
| A3-15 | [serine-proline dipeptide with OH, X=N] | 85 |

Note:
1. ⁀⁀⁀ denotes the place of connection.
2. Positive control (HCV protease inhibitor I (Anaspec) was 1.5 μM.
3. *represents that the two values are from independent experiments of the same compound.

According to Table 9, most of the compounds of A1 to A9 and KA to KC showed significant inhibition of HCV protease with IC$_{50}$ ranging from 5 μM to 27 μM. For other compounds showing less inhibitive activities, they were still useful in treating or prophylaxis of HCV infection as long as the amount was large enough.

Example 3

New Compound (Formula (XIII)) Isolated from the Mycellium of *Antrodia cinnamomea*

Figure 2:
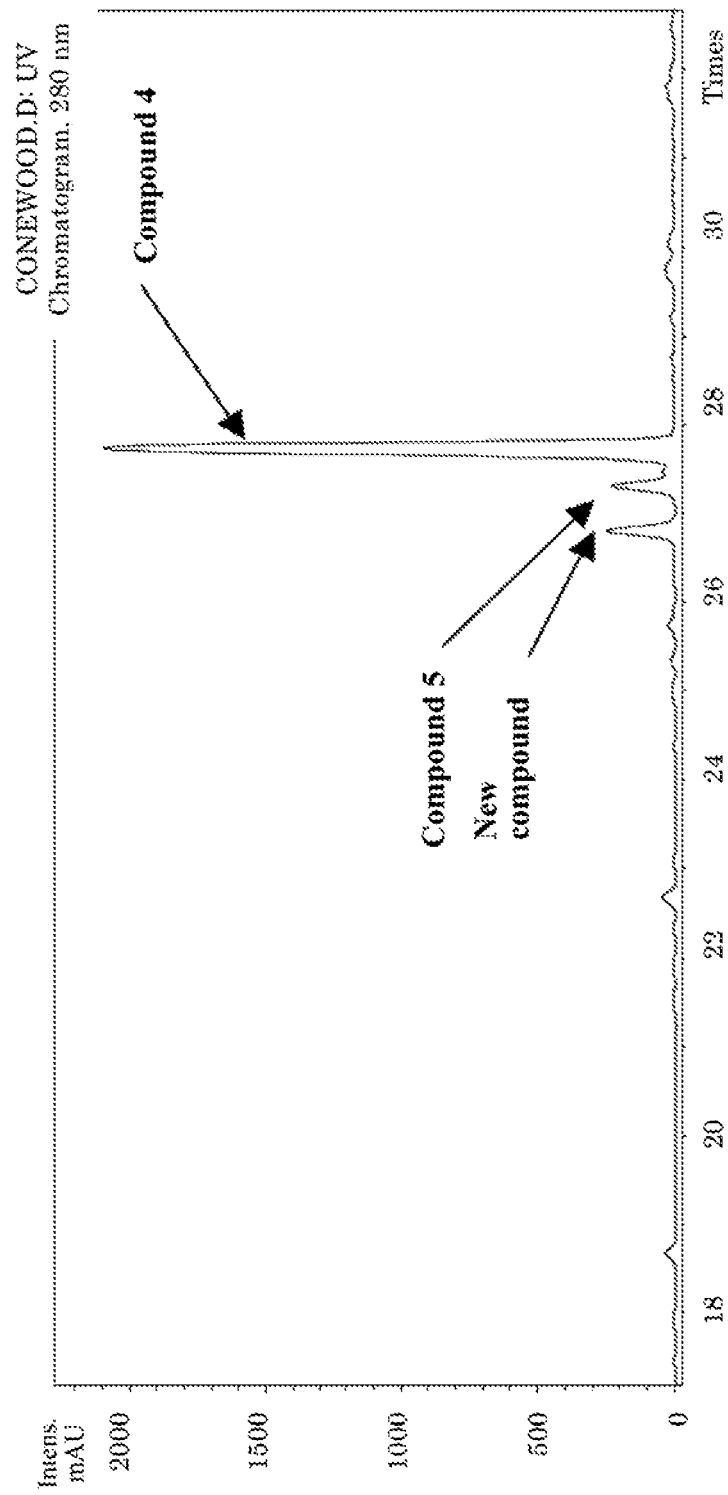
FIG. 2 shows the HPLC chromatogram of Fr. 12.
Figure 3:
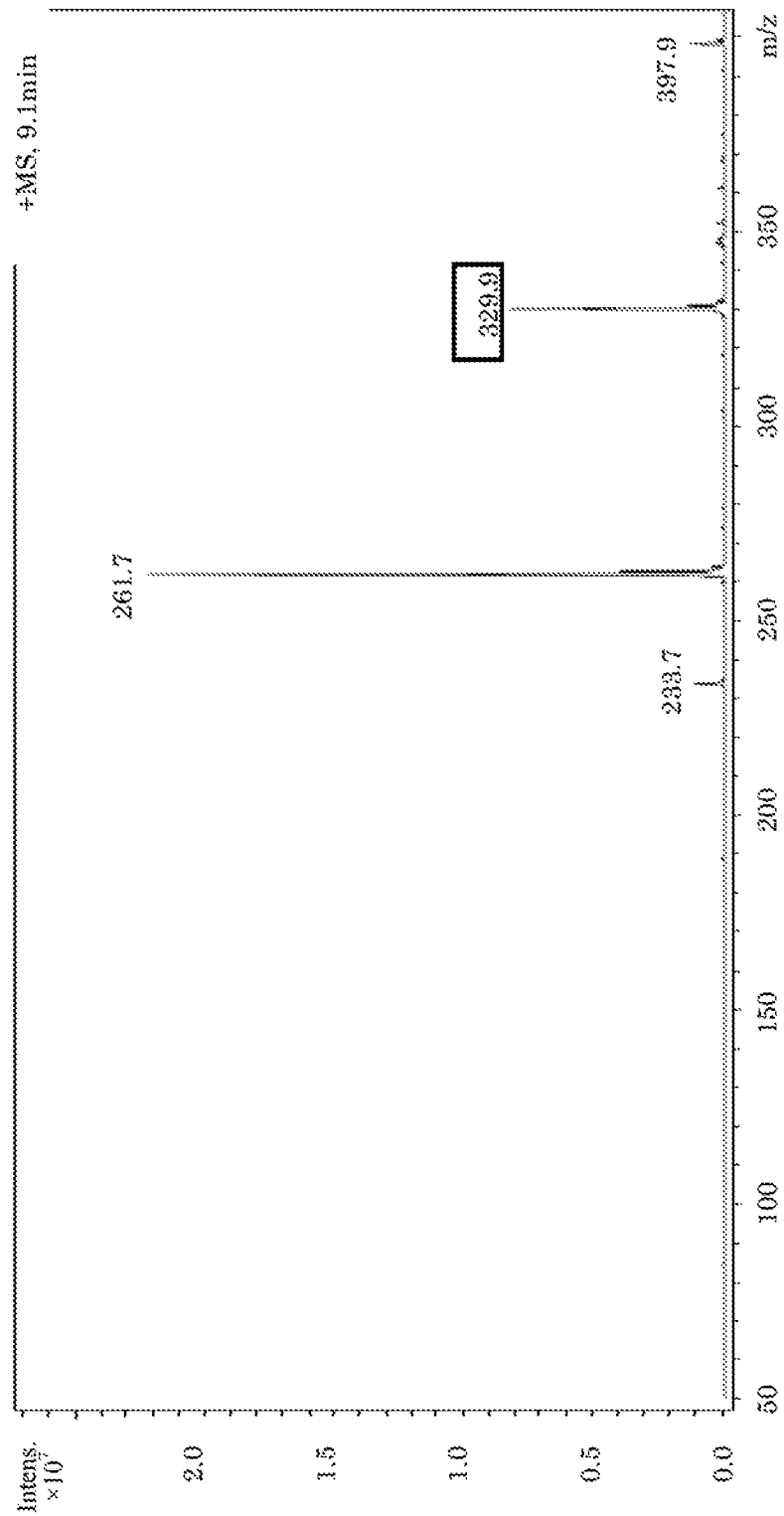
FIG. 3 shows MS spectrum of a compound of formula (XIII).

The EtOH extract was prepared from the mycelium of *Antrodia cinnamomea* (450 g). The extract was separated by silica gel column chromatography, and it was divided into Fr.1-Fr.10. Moreover, Fr.9 which contained Compound 4 was separated by silica gel column chromatography to obtain Fr.12. Fr.12 was analyzed by LC-MS. The new compound, together with known Compounds 4 and 5, were confirmed after HPLC isolation (FIGS. 1-3).

The new compound was isolated as a yellow oily compound with molecular formula: $C_{19}H_{23}O_4N$ ([M]$^+$ m/329.16271, HR-EI-MS), specific rotation: $[\alpha]_{23}^D$ ±0° (c 0.276, CHCl$_3$). The UV spectrum showed the maximum wavelength of absorption at 280 nm, suggesting the presence of phenyl ring(s) in the molecule. Moreover, according to the IR spectral analysis, a hydroxyl group (3019 cm$^{-1}$) and carbonyl group (1714 cm$^{-1}$) were also predicted to be present.

Figure 4:
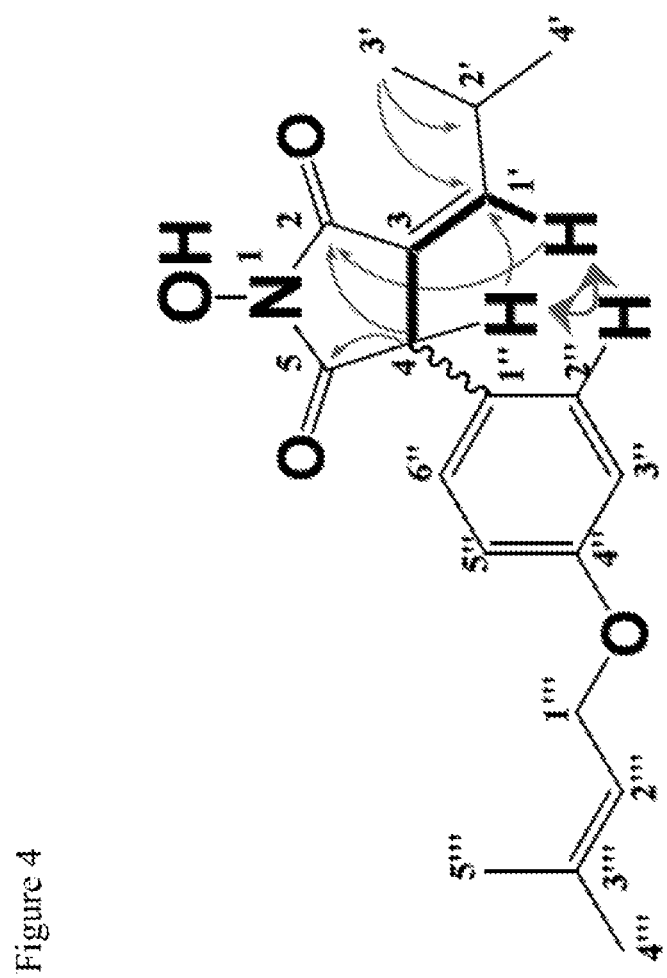
FIG. 4 shows 2D NMR correlations for a compound of formula (XIII). Heavy line: $^1$H-$^1$H COSY; One-way arrow: HMBC related; Two-way arrow: NOE related. The curve line means that the compound of formula (XIII) is a racemic mixture of (4S)- and (4R)-[4-(3-methyl-2-butenyloxy)phenyl]derivatives with a 1:1 ratio. This was confirmed by the optical rotation value $[\alpha]_D = 0$.

The structure of new compound was finally determined by $^1$H-NMR, $^{13}$C-NMR (Table 11) and HMBC, HMQC spectra (FIG. 4).

TABLE 11

$^1$H-NMR and $^{13}$C-NMR spectral data of a new compound (300 MHz and 75 MHz, respectively) in CDCl$_3$

| Position | δ$_H$ | δ$_C$ |
|---|---|---|
| 1 | — | — |
| 2 | — | 167.0 |
| 3 | — | 150.0 |
| 4 | 4.38 (d, J = 2.0 Hz) | 46.2 |
| 5 | — | 171.2 |
| 1' | 6.77 (d, J = 8.8, 2.0 Hz) | 148.5 |
| 2' | 2.24-2.30 (m) | 28.8 |
| 3' | 0.72 (d, J = 6.6 Hz) | 21.5 |
| 4' | 0.99 (d, J = 6.6 Hz) | 20.6 |
| 1" | — | 119.3 |
| 2" | 7.15 (d, J = 8.8 Hz) | 129.0 |

TABLE 11-continued

1H-NMR and 13C-NMR spectral data of a new compound (300 MHz and 75 MHz, respectively) in CDCl$_3$

| Position | δ$_H$ | δ$_C$ |
| --- | --- | --- |
| 3" | 6.88 (d, J = 8.8 Hz) | 115.3 |
| 4" | — | 159.0 |
| 5" | 6.88 (d, J = 8.8 Hz) | 115.3 |
| 6" | 7.15 (d, J = 8.8 Hz) | 129.0 |
| 1''' | 4.48 (d, J = 6.3 Hz) | 64.8 |
| 2''' | 5.44-5.47 (m) | 119.3 |
| 3''' | — | 139.4 |
| 4''' | 1.79 (s) | 18.3 |
| 5''' | 1.73 (s) | 25.8 |

The structure of a new compound was shown as formula (XIII).

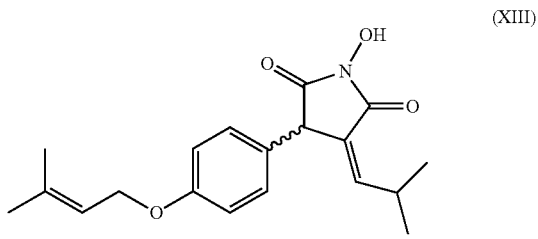 [SMILES: CC(C)=CCOc1ccc(C2C(=O)N(O)C(=O)/C2=C\C(C)C)cc1]

(XIII)

Figure 5:
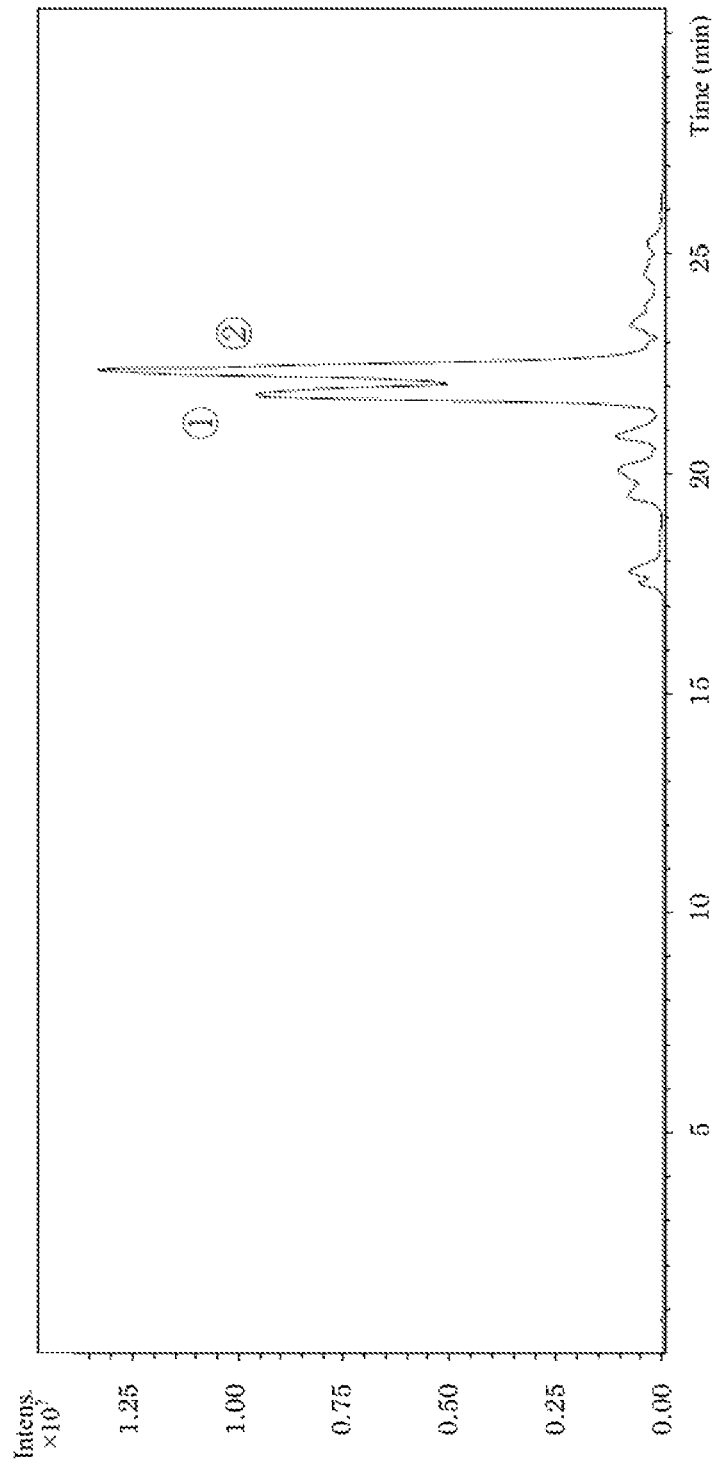
FIG. 5 shows the chromatogram of a compound of formula (XIII) with a chiral column. Column: SHISEIDO FINE CHEMICALS Chiral CD-Ph Packed Column (4.6 i.d.×250 mm) Temperature: 30° C.; shift layer: $CH_3CN$-0.1% Acetic acid=20:80→100:0; flow speed: 0.5 mL/min, detection: ESI-MS(+).
Figure 6:
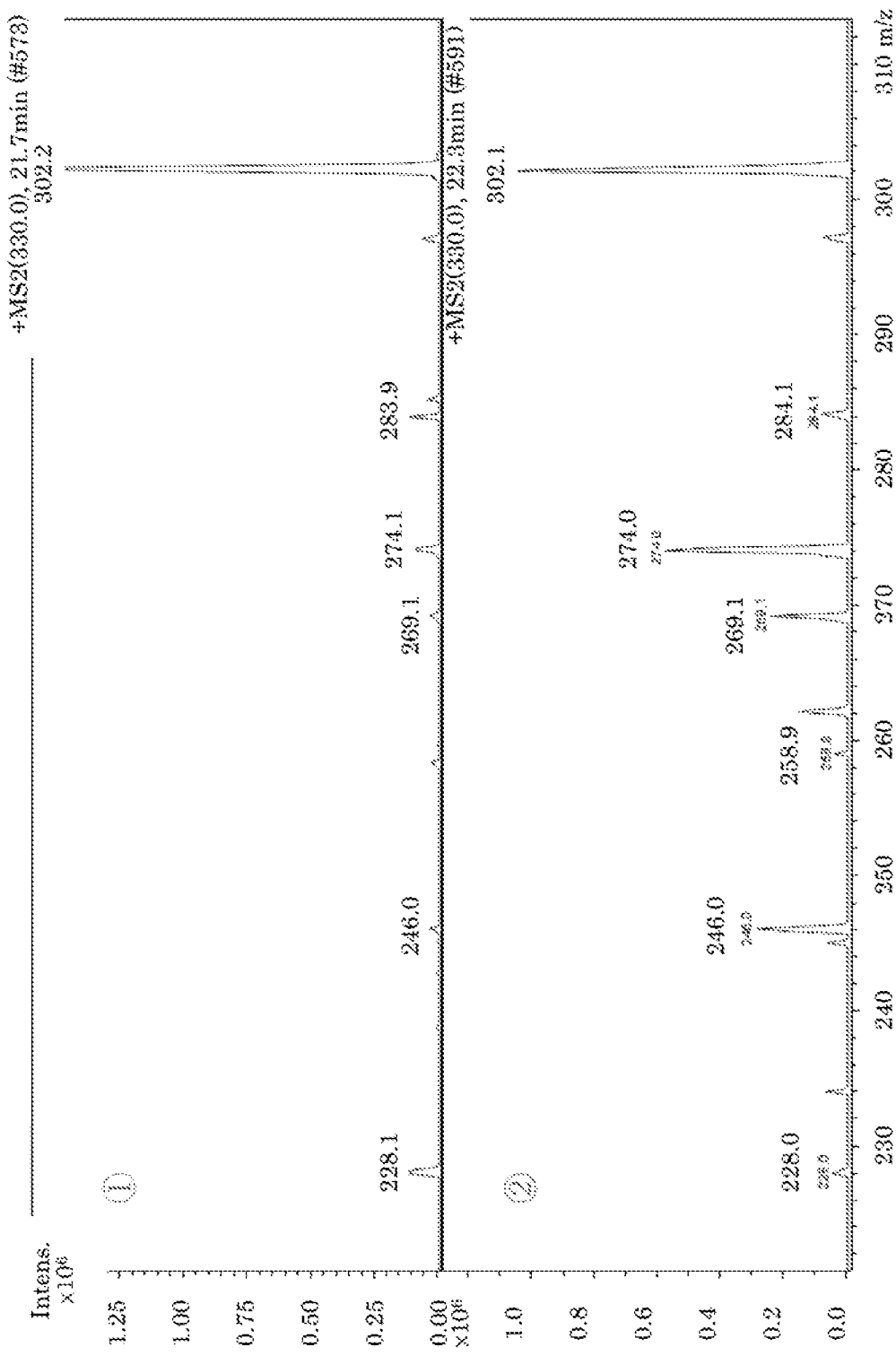
FIG. 6 shows MS² spectra for both peaks.

According to the HPLC analysis with a chiral column, a compound of formula (XIII) was showed two peaks with very close retention-times (FIG. 5). The MS$^2$ spectral pattern at m/z 330 in the MS (MS$^1$) spectra were essentially identical with each other (FIG. 6).

On the basis of the specific optical rotation value: $[\alpha]_D^{23}$ ±0°, the compound of formula (XIII) was confirmed as a racemic form. Thus, the curve line indicated that the compound of formula (XIII) was a racemic mixture of (4S)- and (4R)-[4-(3-methyl-2-butenyloxy)phenyl]derivatives with a 1:1 ratio. In addition, appreciable Nuclear Overhauser Effect (NOE) was found between H-1' and H-4, showing that an exo-cyclic double bond is located at C-1' and C-3 with a Z-type.

A new compound of formula (XIII) with a double bond in the side chain was isolated from the mycelium of *Antrodia cinnamomea* by extracting with EtOH, and the structure was determined by spectroscopic means. For verification, powder of mycelium of *Antrodia cinnamomea* was extracted with a different organic solvent CHCl$_3$ and analyzed by LC-MS in the same way. The same peak was confirmed (data not shown). These findings showed that the compound of formula (XIII) was able to be extracted with both solvents, there was no big difference between CHCl$_3$ and EtOH extractions.

Example 4

NS3/4A HCV Protease Inhibition Assay for Determining Inhibitive Activity of a Compound of Formula (XIII)

When sensitive cells were infected with HCV virus, some precursor proteins were translated from uncoated virus RNA in the cytoplasm. According to the protease, the precursor proteins were processed into different viral proteins. Among viral proteins, NS3, a serine protease and RNA helicase, was an important non-structural protein involved in virus protein maturation and virus genome replication.

Figure 7:
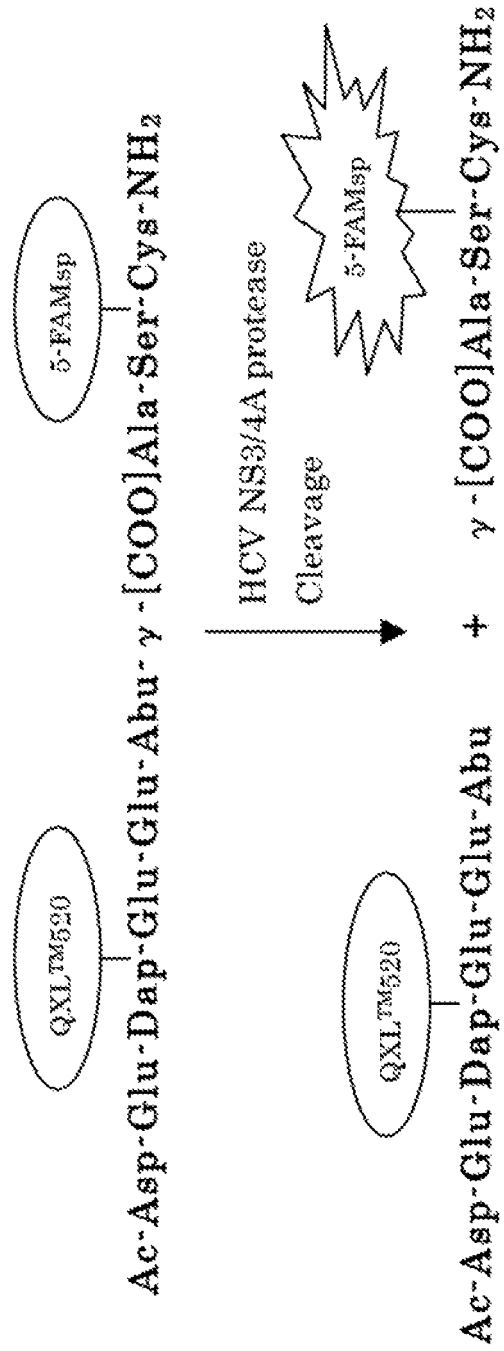
FIG. 7 shows principles of NS3/4A HCV protease inhibition assay. Fluorescence was generated when 5-FAMsp was cleaved. The fluorescence intensity was detected.

In this assay, protein (FRET) was prepared and modified with fluorescent protein 5-FAM as a substrate and QXL™ 520 as a quencher. The substrate was incubated with NS3/4A HCV protease and testing samples, and the fluorescence intensity was measured, according to the mechanism shown in FIG. 7 (C. M. Ma, Y. Wei, Z. G. Wang and M. Hattori: Triterpenes from *Cynomorium Smngaricium*-analysis of HCV Protease Inhibitory Activity, Quantification and Content Change Under the Influence of Heating. *J. Nat. Med.*, 63, 9-14, 2009). In this assay, HCV NS3 Protease inhibitor 2 was used as positive control.

Result:

For the compound of formula (XIII), a 50% NS3/4A HCV protease inhibitory concentration (IC$_{50}$) was shown in Table 12.

TABLE 12

NS3/4A HCV protease inhibitive activity of a compound of formula (XIII)

| Sample | Structure | IC$_{50}$ (μM) |
| --- | --- | --- |
| Antrodin F | (structure shown) | 8.7 |
| Positive control | HCV NS3 Protease Inhibitor 2 | 1.9 |

Example 5

HIV-1 Protease Inhibition Assay for Determining Inhibitive Activity of a Compound of Formula (XIII) and Compounds 1-5

HIV was a retrovirus with a single-stranded RNA genome. HIV protease was an important enzyme for replication. Translated proteins in the host cell were cut into the desired shape by the enzyme. The substance was a protein dimer consisting of 99 amino acids, and the active center was Asp residues.

In this assay, oligopeptide (His-Lys-Ala-Arg-Val-Leu-Phe (NO2)-Glu-Ala-NLe-Ser-NH2) with strengthened absorbance was prepared as a substrate, in which para site of Asp residue was modified by nitro. The substrate was incubated in the presence of HIV-1 protease and the test samples. Generation ratio of hydrolysis product (Phe (NO2)-Glu-Ala-NLe-Ser-NH2) was analyzed by HPLC, and the HIV-1 inhibitory activity in test sample was detected (Y. Wei, C. M. Ma, D. Y. Chen and M. Hattori: Anti-HIV-1 Protease Triterpenoids from *Stauntonia Obovatifoloala Hayata* Subsp. Phytochemistry, 69, 1875-1879, 2008). In this assay, pepsatatin A was used as a positive control.

Result:

The inhibitory activity of a compound of formula (XIII) and compounds 1-5 (U.S. Pat. No. 7,109,232), ingredients in the mycelium of *Antrodia cinnamomea*, was represented as a 50% inhibitory concentration ($IC_{50}$) against HIV-1 protease (Table 13).

TABLE 13

HIV-1 protease inhibitive activity of a compound of formula (XIII) and compounds 1-5

| Sample | Structure | | $IC_{50}$ (μM) |
|---|---|---|---|
| Compound 1 | 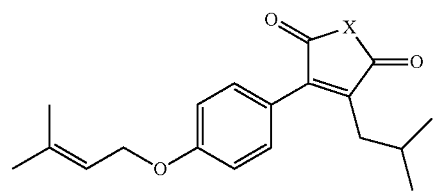 | X=O | >300 |
| Compound 2 | | X=NH | 54 |
| Compound 3 | | X=N—OH | 6.5 |
| Compound 4 | 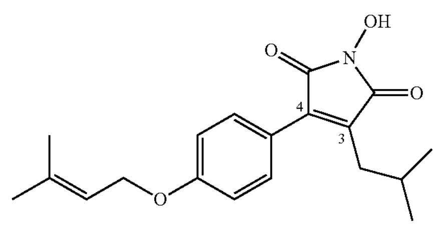 [SMILES: CC(C)=CCOc1ccc(C2=C(CC(C)C)C(=O)N(O)C2=O)cc1] | 3R*, 4S* | 4.4 |
| Compound 5 | | 3R*, 4R* | 198.3 |
| (Compound of formula (XIII)) | | — | 16.6 |
| Positive control | Pepsatin | — | 0.5 |

Compound 4 showed the highest inhibitory activity, followed by compound 3, which was followed by a compound of formula (XIII) and compound 2. Compound 5 was a structural isomer of compound 4, but it showed different activity between them. Although activity of compound 1 was lowest, compound 1 was useful in treating or prophylaxis of HIV infection as long as the amount was large enough.

What is claimed is:

1. A compound having formula (II),

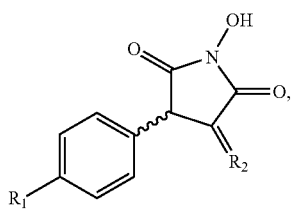

(II)

wherein $R_1$ is $C_{1-10}$ alkyloxy, $C_{2-10}$ alkenyloxy, or $C_{2-10}$ alkynyloxy; and $R_2$ is $C_{1-10}$ alkyl or $C_{2-10}$ alkenyl, or pharmaceutically acceptable salts or prodrugs thereof.

2. The compound of claim 1, wherein the compound is

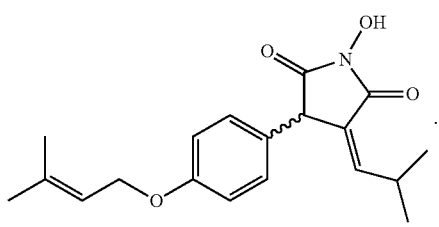 [SMILES: CC(C)=CCOc1ccc(C2C(=O)N(O)C(=O)/C2=C\C(C)C)cc1]

(XIII)

3. A method for treating or prophylaxis of hepatitis C virus (HCV) infection which comprises administering to a subject in need thereof an effective amount of a compound having the formula (II)

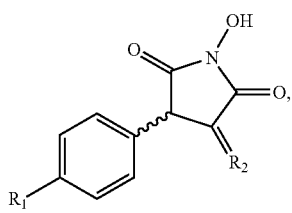

(II)

wherein
$R_1$ is $C_{1-10}$ alkyloxy, $C_{2-10}$ alkenyloxy, or $C_{2-10}$ alkynyloxy; and $R_2$ is $C_{1-10}$ alkyl or $C_{2-10}$ alkenyl.

4. The method of claim 3, wherein the compound is

5. The method of claim 3, wherein the subject is a mammal.
6. The method of claim 5, wherein the mammal is a human.
7. A method for treating or prophylaxis of human immunodeficiency virus (HIV) infection which comprises administering to a subject in need thereof an effective amount of a compound having the formula (II)

(II)

wherein
$R_1$ is $C_{1-10}$ alkyloxy, $C_{2-10}$ alkenyloxy, or $C_{2-10}$ alkynyloxy; and
$R_2$ is $C_{1-10}$ alkyl or $C_{2-10}$ alkenyl.

8. The method of claim 7, wherein the compound is (XIII)

9. The method of claim 7, wherein the subject is a mammal.
10. The method of claim 9, wherein the mammal is a human.

* * * * *

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: protease substrate
<220> FEATURE:
<221> NAME/KEY: MISC_FEATURE
<222> LOCATION: (1)..(1)
<223> OTHER INFORMATION: Xaa = Ac-Asp, N-acetylaspartic acid
<220> FEATURE:
<221> NAME/KEY: MISC_FEATURE
<222> LOCATION: (3)..(3)
<223> OTHER INFORMATION: Xaa = Dap(QXLTM520), 2,3-Diaminopropionic acid
      conjugated with dye QXLTM520
<220> FEATURE:
<221> NAME/KEY: MISC_FEATURE
<222> LOCATION: (6)..(6)
<223> OTHER INFORMATION: Xaa = Abu, Aminobutyric acid; amide bond
      between the Abu at position 6 and the Ala at position 7 is
      replaced with an ester bond
<220> FEATURE:
<221> NAME/KEY: MISC_FEATURE
<222> LOCATION: (9)..(9)
<223> OTHER INFORMATION: Xaa = Cys(5-FAMsp)-NH2, cysteine amide
      conjugated with 5-FAMsp

<400> SEQUENCE: 1

Xaa Gly Xaa Gly Gly Xaa Ala Ser Xaa
1               5

<210> SEQ ID NO 2
<211> LENGTH: 11
<212> TYPE: PRT
<213> ORGANISM: Artificial Sequence
<220> FEATURE:
<223> OTHER INFORMATION: protease substrate
<220> FEATURE:
<221> NAME/KEY: MISC_FEATURE
<222> LOCATION: (7)..(7)
<223> OTHER INFORMATION: Xaa = Phe(NO2), nitrophenylalanine
<220> FEATURE:
<221> NAME/KEY: MISC_FEATURE
<222> LOCATION: (10)..(10)
<223> OTHER INFORMATION: Xaa = Nle, norleucine
<220> FEATURE:
<221> NAME/KEY: MISC_FEATURE
<222> LOCATION: (11)..(11)
<223> OTHER INFORMATION: Xaa = Ser-NH2, serine amide

<400> SEQUENCE: 2

His Lys Ala Arg Val Leu Xaa Gly Ala Xaa Xaa
1               5                   10

<210> SEQ ID NO 3
<211> LENGTH: 5
<212> TYPE: PRT
<213> ORGANISM: Artificial Sequence
<220> FEATURE:
<223> OTHER INFORMATION: protease substrate hydrolysis product
<220> FEATURE:
<221> NAME/KEY: MISC_FEATURE
<222> LOCATION: (1)..(1)
<223> OTHER INFORMATION: Xaa = Phe(NO2), nitrophenylalanine
<220> FEATURE:
```

```
<221> NAME/KEY: MISC_FEATURE
<222> LOCATION: (4)..(4)
<223> OTHER INFORMATION: Xaa = Nle, norleucine
<220> FEATURE:
<221> NAME/KEY: MISC_FEATURE
<222> LOCATION: (5)..(5)
<223> OTHER INFORMATION: Xaa = Ser-NH2, serine amide

<400> SEQUENCE: 3

Xaa Gly Ala Xaa Xaa
1               5
```